(12) United States Patent
Ginsburg

(10) Patent No.: US 10,573,407 B2
(45) Date of Patent: Feb. 25, 2020

(54) MEDICAL SERVICES TRACKING SERVER SYSTEM AND METHOD

(71) Applicant: Leonard Ginsburg, Merion, PA (US)

(72) Inventor: Leonard Ginsburg, Merion, PA (US)

( * ) Notice: Subject to any disclaimer, the term of this patent is extended or adjusted under 35 U.S.C. 154(b) by 61 days.

(21) Appl. No.: 15/204,900

(22) Filed: Jul. 7, 2016

(65) Prior Publication Data

US 2016/0321404 A1   Nov. 3, 2016

Related U.S. Application Data

(63) Continuation-in-part of application No. 14/666,278, filed on Mar. 23, 2015, now Pat. No. 10,319,468.

(Continued)

(51) Int. Cl.
*G16H 10/60* (2018.01)
*G06F 19/00* (2018.01)
(Continued)

(52) U.S. Cl.
CPC ......... *G16H 10/60* (2018.01); *G06F 3/04817* (2013.01); *G06F 3/04842* (2013.01);
(Continued)

(58) Field of Classification Search
CPC ...... G06Q 50/22; G06Q 50/24; G06F 19/322; G06F 19/324; G06F 19/327;
(Continued)

(56) References Cited

U.S. PATENT DOCUMENTS

2006/0064020 A1   3/2006   Burnes et al.
2009/0265188 A1*  10/2009  Lamy ................. G06F 3/04817
                                                                    705/3
(Continued)

FOREIGN PATENT DOCUMENTS

| JP | 2017510015 | 4/2017 |
| WO | WO-2015143455 | 9/2015 |
| WO | WO-2018057918 A1 | 3/2018 |

OTHER PUBLICATIONS

"U.S. Appl. No. 15/275,223, Preliminary Amendment filed Mar. 16, 2017", 11 pgs.

(Continued)

*Primary Examiner* — Jonathan Durant
(74) *Attorney, Agent, or Firm* — Moser Taboada

(57) ABSTRACT

Some embodiments include a server system and computer-implemented method for aggregating and tracking medical delivery to a patient. A non-transitory computer-readable medium can include software instructions for a medical services tracking server system and method that upon execution by a server system computing device, patient information from a patient database or server can be received and displayed in a medical record dashboard. A user can view and edit the information, and a user-selectable link can display medical record information. A financial ledger access icon can enable display of financial information related to a procedure. The medical data entry fields can be auto-populated based on a claim or billing signed off by a physician for a medical service or procedure previously provided or performed. Further, the dataflow can include a two-way transfer between the medical data entry field and one or more patient databases, and/or electronic medical records, or servers.

40 Claims, 24 Drawing Sheets

Related U.S. Application Data

(60) Provisional application No. 61/968,693, filed on Mar. 21, 2014.

(51) Int. Cl.
  *G06F 3/0481* (2013.01)
  *G06F 3/0484* (2013.01)
  *G16H 15/00* (2018.01)

(52) U.S. Cl.
  CPC .......... *G06F 19/321* (2013.01); *G06F 19/328* (2013.01); *G16H 15/00* (2018.01)

(58) Field of Classification Search
  CPC ... G06F 19/345; G06F 19/3487; G16H 10/60; G16H 40/20; G16H 15/00
  See application file for complete search history.

(56) References Cited

U.S. PATENT DOCUMENTS

| | | | |
|---|---|---|---|
| 2010/0057646 A1 | 3/2010 | Martin et al. | |
| 2010/0094649 A1* | 4/2010 | White | G06F 19/324 705/2 |
| 2011/0004494 A1* | 1/2011 | Denny, Jr. | G06F 19/328 705/4 |
| 2011/0010192 A1* | 1/2011 | Backhaus | G06F 19/321 705/2 |
| 2011/0202370 A1* | 8/2011 | Green, III | G06F 19/328 705/3 |
| 2011/0276348 A1* | 11/2011 | Ahn | G06F 19/328 705/3 |
| 2011/0301978 A1* | 12/2011 | Shiu | G16H 10/60 705/3 |
| 2012/0078664 A1* | 3/2012 | Hasan | G06F 19/324 705/3 |
| 2012/0130197 A1* | 5/2012 | Kugler | A61B 5/0022 600/300 |
| 2012/0232918 A1* | 9/2012 | Mack | G06F 19/3418 705/2 |
| 2013/0024206 A1 | 1/2013 | Hughes et al. | |
| 2013/0027411 A1* | 1/2013 | Hebler | G06F 19/3418 345/501 |
| 2013/0083185 A1* | 4/2013 | Coleman, III | A61B 3/12 348/78 |
| 2013/0191161 A1* | 7/2013 | Churchwell | G06Q 50/24 705/3 |
| 2013/0290005 A1* | 10/2013 | Vesto | G06Q 50/22 705/2 |
| 2014/0012597 A1 | 1/2014 | Nolte et al. | |
| 2014/0074509 A1 | 3/2014 | Rubendran et al. | |
| 2014/0236631 A1 | 8/2014 | Perrin et al. | |
| 2014/0236635 A1* | 8/2014 | Liberty | G06F 19/322 705/3 |
| 2015/0052032 A1* | 2/2015 | Aharoni | G06Q 10/00 705/30 |
| 2015/0269323 A1 | 9/2015 | Ginsburg | |
| 2016/0063212 A1 | 3/2016 | Monier et al. | |
| 2016/0198996 A1 | 7/2016 | Dullen | |
| 2017/0116373 A1 | 4/2017 | Ginsburg et al. | |

OTHER PUBLICATIONS

"International Application Serial No. PCT/US2015/022091, International Preliminary Report on Patentability dated Sep. 29, 2016", 7 pgs.
"International Application Serial No. PCT/US2015/022091, International Search Report dated Jun. 29, 2015", 3 pgs.
"International Application Serial No. PCT/US2015/022091, Written Opinion dated Jun. 29, 2015", 5 pgs.
"U.S. Appl. No. 14/666,278, Non Final Office Action dated Jan. 9, 2018", 22 pgs.
"U.S. Appl. No. 14/666,278, Non Final Office Action dated Dec. 21, 2017", 20 pgs.
"U.S. Appl. No. PCT/US2017/052993, International Search Report dated Dec. 1, 2017", 2 pgs.
"International Application Serial No. PCT/US2017/052993, Written Opinion dated Dec. 1, 2017", 9 pgs.
Placement of Inventor work by MD Office in "EyeNet Extra" distributed as a Supplement to an EyeNet magazine available in Oct. 2014 at the American Academy of Ophthalmology (AAO) 2014 conference Oct. 18-21, 2014.

\* cited by examiner

Current Complaints —430

Patient insurance —401
Referring doctor —402
Primary care physician —403

—405 High deductible plan
Patient balance: —406 Days left post op period

404 — Today's Examination
Return Visit —434

465 — Information alert

432 —
425 —
500 —
450 —
700 —
475 —
490 —
460 —

Retina Flowsheet

Problems —600 · All ○ Active Surgeries

| Entered Timeline | ICD | Location | Diagnosis | Timeline | Procedure | Description |
|---|---|---|---|---|---|---|
| DATE | | OU | | | | |
| DATE | | | | | | |
| DATE | | OS | | | | |

Summary: —800

| Date | Procedure OD | Procedure OS | Provider | Unit | Office Visit | OCT OD | OCT OS | FA OD | FA OS | ICG OD | ICG OS | Photo OU AF | Location | Surgeon | Comments | Extended Opth OD | Extended Opth OS | VF OD | VF OU | VF OS | VA OD | VA OS | Other | Notes |
|---|---|---|---|---|---|---|---|---|---|---|---|---|---|---|---|---|---|---|---|---|---|---|---|---|
| 12/29/14 | | Drug name | 2RP | 5 | | | | | ⊙ | | | | | | | | | | | | | | | ☐ |
| 11/17/14 | | Drug name | 2RP | 5 | | ⊙⊠ | | Billing | | | | | | | | | | | | | | | | ☐ |
| 10/6/14 | | Drug name | 2RP | 5 | | ⊙⊠ | | ⊙ | | | | | | | | | | | | | | | | ☐ |
| 8/14/14 | | Drug name | 2RP | 1 | | ⊙⊠ | | ⊙ | | | | | | | | ✓ | | | | | | | | ☐ No Modifier |
| 6/26/14 | Drug name | | DVR | 1 | | ✓ | | | | | | | | | | ✓ | | | | | | | | ☐ |
| 6/16/14 | Drug name | | DVR | 1 | | ✓ | | | | | | | | | | | | | | | | | | |

407 — ☐ Letters or Results from outside

408 — ☐ Letters sent

423 — ☐ Orders

409 — ☐ Today's history

411 — ☐ Today's plan

413 — ☐ Today's billing

Autopopulate into plan or order screen in EMR

415 — National Patient Registry

417 — ☐ Hospital EMR

421 — ☐ Take you to Eprescribe

419 — ☐ Imaging center —424a

436 — ☐ Correspondence —424b

FIG. 4A

Current Complaints — 430

Patient insurance — 401
Referring doctor — 402
Primary care physician — 403
Patient balance: — 
Today's Examination — 404, 432
Return Visit — 434

425 — 600 — 610 — 475 — 630 — 640 — 650 — 450 — 710 — 720 — 730 — 400

| Retina Flowsheet | | | | | | | |
|---|---|---|---|---|---|---|---|
| Problems — 620 | | | | ⦿All ○Active | Surgeries | | |
| Entered | Timeline | ICD | Location | Diagnosis | Timeline | Procedure | Description |
| DATE | | | OU | | | | |
| DATE | | | | | 855 | | 870 |
| DATE | | | OS | | 860 | | 874 |

Summary: 810 — 820 — 830 — 840 — 845 — 850 — 872 — 882 — 880

800 — 805

| Date | Procedure | | Provider | Unit | Office Visit | OCT | | FA | | ICG | |
|---|---|---|---|---|---|---|---|---|---|---|---|
| | OD | OS | | | | OD | OS | OD | OS | OD | OS |
| DATE | 815 | Drug name | 2RP | 5 | | | | ⓘ | ⓘ | | |
| DATE | | Drug name | 2RP | 5 | | ⓘ🖼 | ⓘ🖼 | | | | |
| DATE | | Drug name | 2RP | 5 | | ⓘ🖼 | ⓘ🖼 | | | | |
| DATE | | Drug name | 2RP | 1 | | ⓘ🖼 | ⓘ🖼 | | | | |
| DATE | Drug name | Drug name | DVR | 1 | | ✓ | ✓ | | | | |
| DATE | | | DVR | 1 | | ✓ | ✓ | | | | |

884 — 885c — 885 — 885a — 885b

407 — ☐ Letters or Results from outside
408 — ☐ Letters sent
423 — ☐ Orders
409 — Today's history
411 — Today's plan
413 — Today's billing Autopopulate into plan or order screen in EMR

430 — Current Complaints

401 — Patient insurance
402 — Referring doctor
403 — Primary care physician
404 — Patient balance: Today's Examination
405 — Return Visit
406 — High deductible plan / Days left post op period
465 — Information alert

Summary
Retina Flowsheet — 425

Problems — 432
| Entered | Timeline | ICD | Location | Procedure OD | OS | Provider | Unit | Office Visit | Diagnosis |
|---|---|---|---|---|---|---|---|---|---|
| | | | OU | | | | | | |
| | | | OU | | | | | | |

450 — ● All  ○ Active Surgeries
| Timeline | Procedure | Description | Location | Surgeon | Comments |
|---|---|---|---|---|---|

482 — 484

Summary: — 500

| Date | Procedure | | Provider | Unit | Office Visit | OCT | | Photo | | FA | | ICG | | VF | | Extended Opth | | VA | | Other | Notes |
|---|---|---|---|---|---|---|---|---|---|---|---|---|---|---|---|---|---|---|---|---|---|
| | OD | OS | | | | OD | OS | OU | AF | OD | OS | OD | OS | OD | OS | OD | OU | OD | OS | | |
| DATE | Drug name | Drug name | LHG | 5 | | ⊙⚠ | ⊙⚠ | | | ⊙⚠ | | | | | | | | | | | ⇦ |
| DATE | Drug name | | LHG | 5 | | ⊙⚠ | ⊙⚠ | | | ⊙⚠ | | | | | | | | 20/40 | 20/30 | | ⇦ |
| DATE | Drug name | | LHG | 1 | | | | | | | | ✓ | | | | | | 20/40 | 20/25 | | ⇦ |
| DATE | | | LHG | 5 | | | | | | | | | | | | | | | | | ⇦ |
| DATE | | | LHG | 5 | | | | | | | | ✓ | | | | | | 20/50 | 20/30 | | ⇦ |
| DATE | | | LHG | 5 | | | | | | | | | | | | | | 20/40 | 20/25 | | ⇦ |
| DATE | | | LHG | 1 | | | | | | | | | | | | | | | | | |

Retina Flowsheet Summary
[Save] [Cancel]

407 — Letters or Results from outside
408 — Letters sent
423 — Orders
409 — Today's history
411 — Today's plan
413 — Today's billing
415 — National Patient Registry
417 — Hospital EMR
421 — Take you to Eprescribe
419 — Imaging center
424a, 424b
436 — Correspondence Autopopulate into plan or order screen in EMR

| Summary | | | | | | | | | | |
|---|---|---|---|---|---|---|---|---|---|---|
| Retina Flowsheet | | | | | | | | | | |
| Problems ● All ○ Active  Surgeries | | | | | | | | | | |
| Entered | Timeline | ICD | Location | Diagnosis | Timeline | Procedure | Description | Location | Surgeon | Comments |
| | | | OU | | | | | | | |
| | | | OU | | | | | | | |

Summary:

| Date | Procedure | | Provider | Unit | Office Visit | OCT | | FA | | ICG | | Photo | | VF | | Extended Opth | | VA | |
|---|---|---|---|---|---|---|---|---|---|---|---|---|---|---|---|---|---|---|---|
| | OD | OS | | | | OD | OS | OD | OS | OD | OS | OU | AF | OD | OS | OD | OU | OD | OS |
| | | | LHG | 5 | 4/20/14 | ◯▲ | ◯▲ | | | | | | | | | 20/40 | 20/30 | 20/40 | 20/30 |
| | | | LHG | 5 | | | | | | | | | | | | | | | |
| | | | LHG | 1 | | | | | | | | | | | | | | | |
| | | | LHG | 5 | 4/20/14 | ◯▲ | ◯▲ | | | | | | | | | | | 20/30 | 20/25 |
| | | | LHG | 5 | | | | | | | | | | | | | | | |
| | | | LHG | 5 | | | | | | | | | | | | | | 20/30 | 20/25 |
| | | | LHG | 5 | 4/20/14 | ◯▲ | ◯▲ | | | | | | | | | | | 20/30 | 20/25 |
| | | | LHG | 5 | | | | | | | | | | | | | | | |
| | | | LHG | 1 | | | | | | | | | | | | | | 20/30 | |

| | A | B | | C | | | | | D | | E | F | G |
|---|---|---|---|---|---|---|---|---|---|---|---|---|---|
| Patient Name | Date Exam | F/U Appt Code | E&M Code | Additional CPT Code | Diagnosis ICD-9 | Colon polyp 45385 | Colon Bx 45380 | Colon Dx 45378 | Upper GI/Bx 43242 | Upper GI/Dx 43235 | Sigmoid oscopy 45330 | Lab Results | BP | Other | Notes | EMR | Mssg | Billing |
| Mr. A | 3.14.15 | | | | | | | | | | | | | | | | | |
| Mr. B | 3.14.15 | | | | | | | | | | | | | | | | | |
| Mr. C | 3.14.15 | | | | | | | | | | | | | | | | | |
| Mr. D | 3.14.15 | | | | | | | | | | | | | | | | | |
| Mr. E | 3.14.15 | | | | | | | | | | | | | | | | | |
| Mr. F | 3.14.15 | | | | | | | | | | | | | | | | | |
| Mr. G | 3.14.15 | | | | | | | | | | | | | | | | | |
| Mr. H | 3.14.15 | | | | | | | | | | | | | | | | | |
| Mr. I | 3.14.15 | | | | | | | | | | | | | | | | | |
| Mr. J | 3.14.15 | | | | | | | | | | | | | | | | | |

Color coded: Green if payment paid, yellow if pending, red if denied

FIG. 12D

| Patient Insurance Name Coverage | Date of Dx of Diabetes | Patient Age | Patient Weight | Patient Height | Body Mass Index | Initial Presenting HbgA1C | Most Recent HgbA1C | Hypertension | Recent BP | All ICD Diagnosis | Medications | Other | Patient Next Appointment | Patient Contact Information | Notes |
|---|---|---|---|---|---|---|---|---|---|---|---|---|---|---|---|
| | | | | | | | | Y/N | | | | | | | |
| | | | | | | | | Y/N | | | | | | | |
| | | | | | | | | Y/N | | | | | | | |
| | | | | | | | | Y/N | | | | | | | |
| | | | | | | | | Y/N | | | | | | | |
| | | | | | | | | Y/N | | | | | | | |
| | | | | | | | | Y/N | | | | | | | |
| | | | | | | | | Y/N | | | | | | | |
| | | | | | | | | Y/N | | | | | | | |
| | | | | | | | | Y/N | | | | | | | |
| | | | | | | | | Y/N | | | | | | | |
| Takes you to patients individual review sheet or can take you anywhere else within chart | | | | | | | | | | | | | Send a message to the patient about anything or allows a note to be written | | |

| Ledger | | | | | | | | | |
|---|---|---|---|---|---|---|---|---|---|
| ServiceTo | Entered | Line | Type | Description | Charge | Payment | WriteOff | Adjustment | Balance |
| 12/1/2014 | 12/1/2014 | 1 | Charge | 92014 Oph Medical Xm&eval Comp | 333.00 | | | | 0.00 |
| 12/1/2014 | 12/1/2014 | 1 | Payment | 2014/12/01 Dep# - 6742 Ozer, He | | 45.00 | | | |
| 12/1/2014 | 12/30/2014 | 1 | Payment | 2014/12/30 Dep# - 8249 Block/CC | | 71.30 | 213.70 | | |
| 12/1/2014 | 12/1/2014 | 2 | Charge | 92134 Cptr Ophth Dx Img Post Seg | 214.50 | | | | 0.00 |
| 12/1/2014 | 12/30/2014 | 2 | Payment | 2014/12/30 Dep# - 8249 Block/CC | | 47.80 | 166.70 | | |
| 12/1/2014 | 12/1/2014 | 3 | Charge | 67028 Injection Eye Drug | 1980.00 | | | | 0.00 |

FIG. 13B

MEDICAL SERVICES TRACKING SERVER SYSTEM AND METHOD

RELATED APPLICATIONS

This application is a continuation-in-part application of U.S. patent application Ser. No. 14/666,278, entitled "MEDICAL SERVICES TRACKING SYSTEM AND METHOD" filed on Mar. 23, 2015, which claims priority from U.S. Provisional Patent Application No. 61/968,693, entitled "PHYSICIAN REVIEW SYSTEM" filed on Mar. 21, 2014, the entire contents of which are incorporated herein by reference.

BACKGROUND

Health care costs in the United States have continued to increase because of the aging of the population, increases in the number of newly insured due to passage of the Affordable Care Act, and a host of other factors driven by fee for service delivery models and waste, administrative inefficiency, mistakes, fraud, etc. In 2013, United States Health care spending reached $2.9 trillion annually, which was approximately 18% of the GDP. As the population ages and average lifespan continues to increase, chronic disease will become more prevalent which leads to increased utilization of the health care system.

While the United States per capita health care spending is among the highest in the world, there are large variations in the quality of care delivered to the population. This creates an unfortunate paradox of high costs compared to other developed countries, but again poorer outcomes on key indicators compared to other developed countries. At the end of the day, the United States consumer is not getting value for the money spent to stay well.

Against this backdrop, Congress passed legislation that emphasized quality and changed how health care is delivered and providers are paid and incentivized e.g., the Physician Quality Reporting System (PQRS) which rewards physicians, who report standardized quality metrics to the Centers for Medicare and Medicaid services (CMS) and penalizes hospitals that don't report these data; the Patient Protection and Affordable Act which implemented requirements driven by value-based payment for health care services, and required that physicians be paid using measures of cost and quality of care by 2017.

With these new laws in place, the Government understood it needed to drive the changes it sought to achieve by fostering the adoption of efficiency measures. Technology was an obvious way to push efficiency throughout the healthcare system. The Health Information Technology for Economic and Clinical Health (HITECH) Act incentivized adoption of EMRs and other technology. This radically changed the health care market as adoption of Electronic Medical Record ("EMR"s) increased dramatically in response to the $36B incentives to purchase Health Information Technology. As a result, many EMR vendors were established and rushed their systems to market with poor user experience. The reaction of physicians to these developments was generally negative. According to a 2014 Medscape survey, 22% of providers are defecting or have never participated in the program, 75% of eligible providers had not yet attested for stage 1 in the year 2013-14. So, while the program was designed to motivate physicians and hospitals to use the technology they bought with the government's assistance, it actually resulted in poor uptake of technology by developers.

That said, EMRs still have been more widely adopted. In essence, these systems provide computerized interfaces between medical professionals and their staff and patient, and have the potential to significantly improve and streamline the business of medical care. The process of summarizing past paper charts and medical history and inputting these data into an EMR system has been challenging. However, when the data are entered, a medical provider can track the delivery of medical care, access a patient's medical records, track billing for services provided, and follow a patient's progress. Because of these benefits, government requirements, and incentives, medical documentation has transitioned from mostly paper records to mostly electronic records over the past decade. According to the Department of Health and Human Services 78% of office based physicians and 59% of Hospitals use a basic electronic medical record or electronic health record.

However, these systems have mostly not met their promise because they typically include complex interfaces that require users to navigate through multiple layers, folders and/or windows to access even basic patient information. As a result, an HIMSS survey showed that 40% of physicians would not recommend their EHR to a colleague, 63.9% said note writing took longer with electronic health records, and 32% were slower to read other clinician's notes. A recent study by Medical Economics indicated that 67% of physicians are displeased with their EHR systems.

An underlying driver of this dissatisfaction is that medical knowledge is doubling every five years, diagnostic tests and procedures are exploding, and documentation requirements for payments are increasing. Doctors are becoming burdened with documentation and administrative tasks rather than spending their time as medical providers. As a result, the EMR system has created a barrier between the doctor and patient, where physicians have to turn their back to the patient to input their findings, and have to navigate through multiple screens to do so rather than interact directly with the patient. The potential of medical errors, over ordering or under ordering of diagnostic tests, and other related mistakes generally occurs because information is missed or buried in the electronic medical record, and/or information does not get transferred from the paper chart. Important laboratory results or reports from other physicians can be lost or are difficult to access.

Another set of problems revolve around finance. Physicians are trained to treat disease and are typically not trained to manage their practices and be business people. As a result, physicians increasingly rely on technicians, assistants, and other staff, often not qualified or properly trained to input information. Improper documentation or billing can occur, which the physician is liable for. Many current EMR systems require significant administrative overhead, and are prone to user error that can result in a discrepancy between billing, claims and payment for professional services and patient procedures. Physicians rarely know if what they had previously authorized to bill was in fact billed correctly, and rarely do physicians know if what they were paid was correct.

To compound the physician's challenge, insurance companies and federal insurance programs such as Medicare and Medicaid hold doctors personally liable for what is billed, paid, and documented. Severe penalties and even criminal charges can occur when errors are made. The government collected $2.5 billion for "wrongful under and over billing and inadequate documentation." (e.g., see https://www.justice.gov/opa/pr/departments-justice-and-health-and-human-services-announce-over-278-billion-returns-joint)

Overall, while EMRs were meant to reduce costs and improve quality of care, the opposite has occurred. Dr. Steven Stack, president of the American Medical Association addressed this issue when he said. "More than half of the physicians who billed Medicare in the United States are currently being penalized 1% of their 2015 payments as a result of the meaningful use program. Imagine, in a world where a 2-year-old can operate an iPhone, graduated physicians are brought to their knees by electronic health records. When you have more than a quarter million physicians being penalized by the Government by a single program, I think that most people will understand the math. It is not that 250,000 plus physicians are the problems, it is most likely the single program they are being punished by."

The overarching problem is that data input and currently available user interfaces are not aligned with the way physicians practice medicine. As Gary Botstein in Decatur, Georgia quotes "It's very easy to record large amounts of data in click off boxes. So, the emphasis is really on data collection but what physicians ought to be doing is data synthesis. They ought to be taking the data, putting it together and coming up a differential diagnosis and then figuring out what the best diagnosis is and then the best treatment. Most systems today are not designed for clinical care. They are set to comply with the Federal Regulations with policy makers as opposed to actual physician care." A solution is needed that helps the physician synthesize information and populate and document the chart when they see a patient on one screen, not on multiple tabs.

In current EMR systems numerous fields and data entry must be placed in many different screens describing physician's findings. It takes a tremendous amount of time for data entry. A wrong click of a mouse can insert the wrong information. A tool is desperately needed that will help a physician review a summary of the patient's history on one screen. Further, the tool should act like a switchboard and enable auto-population of data, where information is documented in a patient's chart when the patient is evaluated. Most EMR systems separate each patient visit by tabs representing each date of service. Critical historic information related to patient testing, diagnosis, surgical histories, and complications are often dispersed on multiple tabs without any visual markers to identify which tab houses the information that a clinician needs to review. These cumbersome formats in the EMR cause significant delay in evaluating a patient and can lead to medical mistakes as information is lost in the confusing formatting. An improved system would provide a snapshot of the critical medical data along with the billing and compliance of the patients' treatment which is unique to existing EMR formats. In combining these critical data into one comprehensive format, the improved system would increase efficiency and accuracy of the patient evaluation process. Accordingly, there is a significant need for a tool that allows a physician to identify medical problems through data visualization, where data is presented and displayed telegraphically, and which enables the rapid identification of billing and collections. Since doctors are typically time constrained, the tool should allow the doctor to access information while examining a patient in order to quickly identify potential billing and or reimbursement problems, as well as medical problems, so that issues can be resolved with the patient in real time. The tool would thus enable the physician to be involved with revenue cycle management, while simultaneously double-checking documentation and reducing medical errors.

Physicians need a tool that will enable them to collect and evaluate their own clinical outcomes. This is important because pay for performance models will be implemented and compensation will be based on clinical and cost savings outcomes, rather than for services and procedures. At the heart of all pay for performance models is data analysis. Tinsley suggests "that tracking clinical data is essential in comparing pay for performance models. Even if a small practice can participate in large scale value based model, it can surely implement measures that track and reward quality patient management. There is always more money behind knowing the clinical outcomes and data behind doctors' requests. A lot of doctors are saving payer's money and not getting a piece of the pie." A tool is desperately needed that can provide the physician with a summary of results of their medical care. This will then enable them to improve care and to negotiate rates with insurance carriers, and will help them in establishing cost saving methods for delivering care and determining if the care they provide meets set standards.

A tool is needed to alert the physician of important messages, letters and laboratory results that are not readily accessible in current EMRs, so they do not miss important findings. Physicians rely on surrogates, like technicians or receptionists to document information on each visit such as a chief complaint. Important alerts that the staff wishes to send to a doctor for a particular day should be communicated on the same page so that everything can be seen. Further, in some cases such alerts should be deleted at the end of the day, because it does not need to be part of a permanent medical record.

The Government has collected substantial sums of money from doctors and hospitals annually for either under or over billing, or wrongful billing. Physicians need a tool that helps them meet all compliance regulations and make certain that charges are billed correctly.

Most EMR systems are highly proprietary and do not communicate well with each other. This lack of interoperability presents a barrier to the transparent communication of health information. A tool is needed that can grab and summarize data from multiple sources and EMR systems. The proposed tool will conform to new interoperability standards proposed and allow for complete patient history no matter what EMR system is used.

Thus, it is recognized in the disclosure herein that allowing physicians to rapidly detect potential problems, inconsistencies, medical changes, potential billing errors, review diagnostic tests and navigate through the entire patient chart history, while enabling centralized access to remote electronic medical records causes a new computing function (e.g., the transmission of a new communication with two-way exchange of up-to-date patient information based on a patient examination on the same day, or during the patient examination, or immediately following the examination) is a technical problem for network communication and other server based technologies.

SUMMARY

Some embodiments include a server system for aggregating and tracking medical delivery to a patient comprising a computing device comprising at least one processor, and a non-transitory computer-readable medium, having stored thereon, software instructions that when executed by the at least one processor of the computing device, cause the computing device to perform operations within a local or consumer device as part of a medical services tracking server system and method. The operations comprise at least associating the local or consumer device with at least one patient database or server, and establishing a dataflow comprising a delivery of patient data for at least one patient within a webpage or display rendered on the local or consumer device. The operations also include displaying at least one medical record dashboard comprising information received or derived from at least one patient database or server. The operations include displaying patient information within one or more windows of at least one medical record dashboard. The one or more windows comprise at least one medical data entry field and at least one financial ledger access icon. The operations include receiving at least a first selection input from a user through the local or consumer device, where upon the first selection input including a selection or activation of the at least one financial ledger access icon, the operations include displaying at least one ledger window comprising financial information related to the at least one medical data entry field, the financial information including at least one of charges, payments, write-offs, adjustments, and balances. Further, the operations include providing a user with view and edit access to at least one medical data entry field, where any of at least one medical data entry field includes a user-selectable link to a medical record display, the medical record display including a user-selectable toggle to the at least one medical record dashboard. The operations also include auto-populating the at least one medical data entry field based at least in part on a claim made or a billing signed off by a physician for at least one medical service or procedure previously provided to or performed on the at least one patient. Further, the dataflow can comprise a two-way transfer from the auto-population of the at least one medical data entry field and the at least one patient database or server.

The operations also include dynamically linking to at least one electronic medical records server system. In some embodiments, the operations cause the computing device to launch the medical services tracking server system and method from a user interface of the electronic medical records server system on a display of the local or consumer device as directed by a user. In some further embodiments, the operations cause the computing device to switch between at least one display generated by the medical services tracking server system and method, and one or more displays generated by the electronic medical records server system.

In some embodiments of the invention, the view and edit access to the at least one medical data field comprises providing a user with an option to update or mark at least one medical data field based on at least one medical diagnosis. In some other embodiments, the update or mark comprises an icon, the icon illustrating a representation of at least one of a worsening diagnosis, a stable diagnosis, or an improving diagnosis. In some further embodiments, the icon comprises a color and/or graphical change providing a visual representation of at least one of items billed, not paid, partially paid or fully paid by insurance, but outstanding amount from patient items not billed, and tests needing reports or interpretations. A simple click will also display a full status of claim reimbursement (patient and insurance).

In some embodiments, the operations cause the computing device to display at least one user-selectable medical record in the medical record display. In some further embodiments, the at least one user-selectable medical record comprises at least one test result or diagnosis. In other embodiments, at least one user-selectable medical record comprises at least one test result or diagnosis from any current procedural terminology code ("CPT code") or any international classification of disease codes version 9 or version 10 ("ICD code"). In some embodiments, the at least one test result or diagnosis comprises an optical coherence tomography ("OCT"), and/or fluorescein angiography ("FA"), and/or indocyanine green chorioangiography ("ICG"), and/or photographic images of a patient's eyes.

Some embodiments comprise the operations causing the computing device to auto-populate the at least one medical data entry field based at least in part on billed, pending or unbilled medical service or procedure previously provided to or performed on at least one patient, data entry found and inputted anywhere else in the EMR system, and/or through a "Digital Imaging and Communications in Medicine" (DICOM) system, and/or from diagnostic or equipment used for treatment. In some embodiments, the at least one patient database or server comprises patient information from a medical provider. In some embodiments, the patient information comprises information received from or derived from a transition of care document or proactive care form. In other embodiments, the patient information comprises information received from or derived from a direct message.

Some embodiments include a computer implemented medical services method comprising providing a server system for aggregating and tracking delivered medical services to a patient, where the server system includes at least one computing device in communication with at least one non-transitory computer-readable medium. The non transitory computer-readable medium includes software instructions stored thereon, that when executed by the computing device, cause the computing device to perform operations within a local or consumer device as part of a medical services tracking server system and method. The operations comprise establishing a dataflow for receiving patient related information from at least one patient database or server, and displaying at least one medical record dashboard comprising a displayed convergence of at least one medical service or procedure and the one or more windows comprising at least one medical data entry field and at least one financial ledger access icon. Some operations of the method include receiving at least a first selection input from a user through the local or consumer device, where upon the first selection input including a selection or activation of the at least one financial ledger access icon, the operations include displaying at least one ledger window comprising financial information related to the at least one medical data entry field, and where the financial information includes at least one of charges, payments, write-offs, adjustments, and balances. Some embodiments include providing a user with view and edit access to the at least one medical data entry field, where any of the at least one medical data entry field can comprise a user-selectable link to a medical record display. The medical record display includes a user-selectable toggle to the at least one medical record dashboard. The operations of the method also include auto-populating the at least one medical data entry field based at least in part on at least one of a claim made or a billing signed off by a physician for at least one medical service or procedure previously provided to or performed on the at least one patient. Further, the dataflow can comprise a two-way transfer from the auto-population of the at least one medical data entry field and the at least one patient database or server.

In some embodiments, the operations of the method cause the computing device to switch between at least one display generated by the medical services tracking server system and method and one or more displays generated by an electronic medical records server system. In some embodiments, the view and edit access comprise providing a user with an option to update or mark at least one medical data field based on at least one medical diagnosis.

In some embodiments, the update or mark comprises an icon illustrating a representation of at least one of a worsening diagnosis, a stable diagnosis, or an improving diagnosis. In some further embodiments, the icon comprises a color or graphical change providing a visual representation of at least one of items billed, items not billed, as well as displaying full status of claim reimbursement (patient and insurance), and tests needing reports or interpretations.

In some embodiments, the operations of the method cause the computing device to display at least one user-selectable medical record in the medical record display. In some further embodiments, the operations of the method cause the computing device to auto-populate the at least one medical data entry field based at least in part on a pending or unbilled medical service or procedure previously provided to or performed on at least one patient.

In some embodiments, the at least one patient database or server comprises patient information from a medical provider. In other embodiments, the patient information comprises information received from or derived from at least one of a transition of care document, a proactive care form, and a direct message. In some further embodiments, the at least one user-selectable medical record comprises at least one test result or diagnosis.

In some embodiments, the at least one test result or diagnosis comprises at least one of optical coherence tomography ("OCT"), or fluorescein angiography ("FA"), and/or indocyanine green chorioangiography ("ICG"), and photographic images of a patient's eyes. In some further embodiments of the invention, the at least one user-selectable medical record comprises at least one test result or diagnosis from any current procedural terminology code ("CPT code") or any international classification of disease codes version 9 or version 10 ("ICD code").

Some embodiments include a system or method where the operations cause the computing device to display an instant message field configured to communicate information to the user. Some embodiments include a system or method where any of the operations can include a self-destruct feature configured and arranged to erase any previously displayed information after a specified time period.

In some embodiments of the invention, the operations of the system or method cause the computing device to auto-populate the at least one medical data entry field with information associated with at least a patient treatment or treatment summary, a diagnosis or diagnosis summary, patient feedback or a patient feedback summary, and/or other physician or other medical professional summaries or patient records.

In some embodiments, the operations of the system or method cause the computing device to calculate at least one patient outcome based at least in part on patient information from a patient treatment or treatment summary, a diagnosis or diagnosis summary, patient feedback or a patient feedback summary, and/or other physician or other medical professional summaries and patient records. In some further embodiments, the at least one patient outcome comprises one or more physician quality reporting system (PQRS) quality measures.

DESCRIPTION OF THE DRAWINGS

FIG. 2 illustrates a medical record window of the medical record system useful for deploying or launching embodiments of the invention described herein.

FIG. 4A illustrates a medical record dashboard in accordance with some embodiments of the invention.

FIG. 4B illustrates a portion of the medical record dashboard of FIG. 4A in accordance with some embodiments of the invention.

FIG. 4D illustrates a portion of the medical record dashboard of FIG. 4A in accordance with some embodiments of the invention.

FIG. 5A depicts a medical summary update process in accordance with some embodiments of the invention.

FIG. 5B illustrates a notes update process in accordance with some embodiments of the invention.

FIG. 6 illustrates a user action record access process in accordance with some embodiments of the invention.

FIG. 8 illustrates a medical record and diagnosis update process in accordance with some embodiments of the invention.

FIG. 10A illustrates a medical record update marker process in accordance with some embodiments of the invention.

FIG. 10B illustrates a medical record update marker process in accordance with some embodiments of the invention.

FIG. 11 illustrates a portion of the medical record dashboard of FIG. 4A including a scrolled display in accordance with some embodiments of the invention.

FIG. 12A illustrates a portion of the medical record dashboard in accordance with another embodiment of the invention.

FIG. 12D illustrates a portion of a medical record dashboard for display as a function of patients seen during a certain period of time with CPT codes performed in accordance with some embodiments of the invention.

FIG. 12E illustrates a portion of a medical record dashboard for display as a function of patients with a specific disease ICD in accordance with some embodiments of the invention.

FIG. 13A illustrates a medical record dashboard in accordance with some embodiments of the invention.

FIG. 13B illustrates a ledger window accessible from the medical record dashboard of FIG. 13A in accordance with some embodiments of the invention.

DETAILED DESCRIPTION

Figure 1:
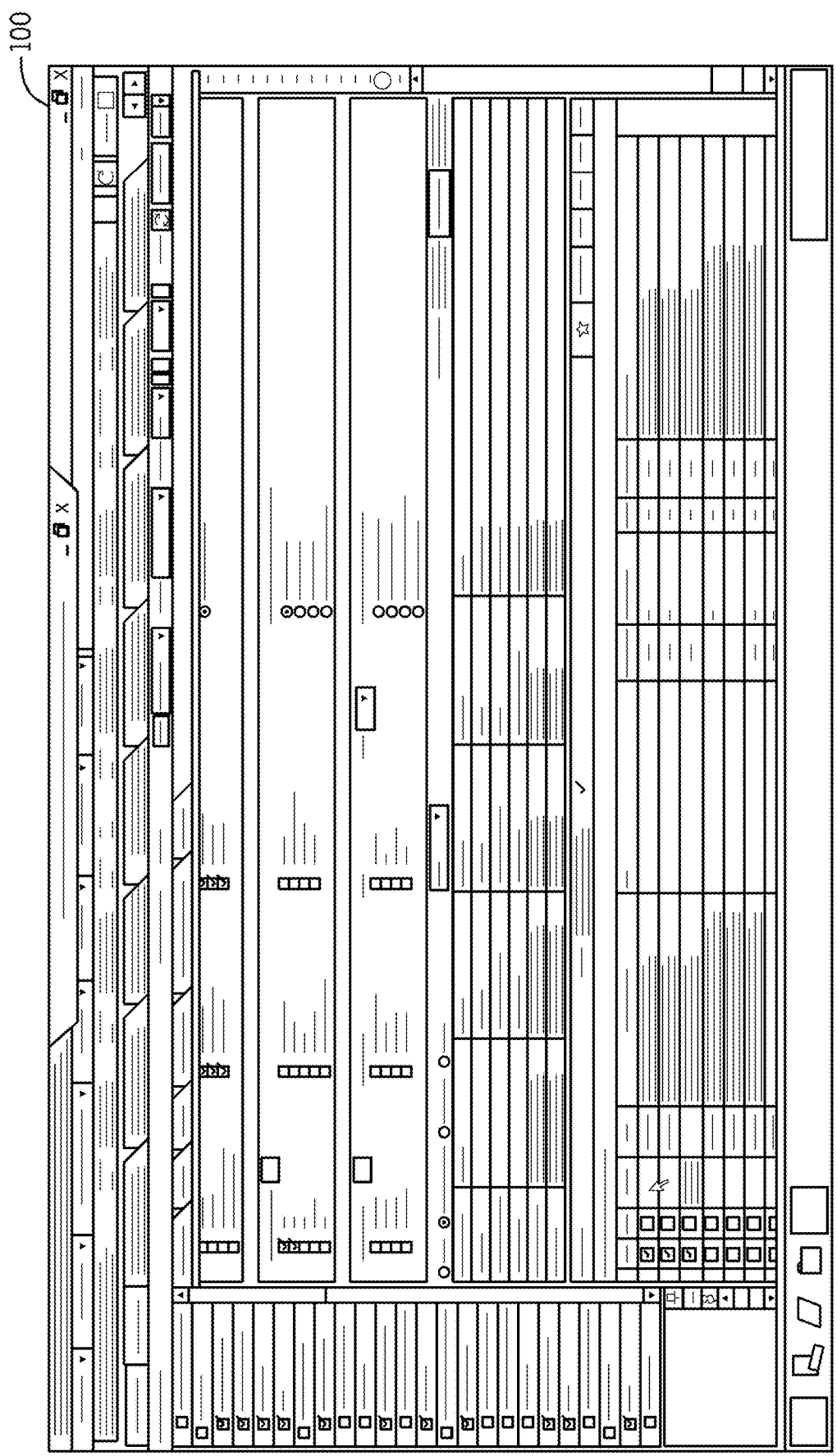
FIG. 1 illustrates a sample medical record system useful for deploying or launching embodiments of the invention described herein.

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless specified or limited otherwise, the terms "mounted," "connected," "supported," and "coupled" and variations thereof are used broadly and encompass both direct and indirect mountings, connections, supports, and couplings. Further, "connected" and "coupled" are not restricted to physical or mechanical connections or couplings.

The following discussion is presented to enable a person skilled in the art to make and use embodiments of the invention. Various modifications to the illustrated embodiments will be readily apparent to those skilled in the art, and the generic principles herein can be applied to other embodiments and applications without departing from embodiments of the invention. Thus, embodiments of the invention are not intended to be limited to embodiments shown, but are to be accorded the widest scope consistent with the principles and features disclosed herein. The following detailed description is to be read with reference to the figures, in which like elements in different figures have like reference numerals. The figures, which are not necessarily to scale, depict selected embodiments and are not intended to limit the scope of embodiments of the invention. Skilled artisans will recognize the examples provided herein have many useful alternatives that fall within the scope of embodiments of the invention.

Some embodiments herein provide one or more technological solutions in the realm of one or more of data assimilation and recordation with real-time communications across a network, computers, or the Internet to improve the performance of, and technology of, data assimilation and recordation, communication and messaging software, systems and servers by providing automated functionality that effectively and more efficiently manages data assimilation and recordation and related automatic triggering of new computing events in the network based on said data gathered during an actual event in ways that cannot effectively be done, or done at all, manually. For example, some embodiments herein provide one or more technological solutions to processing a user interface including a single page quick review "summary sheet" that is rendered by pulling key data points from EMR interactive notes allowing a doctor to provide the best possible care. Further, the improved assimilation and recordation, communication and messaging software, and systems and servers enable centralized collection and review of information and two-way auto-population of the user interface from billing or other parts of local and remote electronic medical record systems that can reduce human error, and can cut down on medical errors. This technology can allow a doctor or other healthcare worker to quickly access and review critical medical and compliance data using consistent data visualization field formats. This technology can automatically summarize each patient visit on one line on one page that can be seen and through pattern recognition, and rapidly visualized. This technology can allow a doctor to instantly evaluate a patient's situation, and catch potential billing errors.

Some embodiments herein provide one or more technological solutions to providing a user interface that functions as a "command center" for the physician's decision-making. Using data collection, assimilation and recordation with real-time communications across a network, computers, or the Internet, some embodiments of the invention described herein provide an information hub where the lifetime of a patient's medical and surgical history, diagnostic tests results, and prescribed medications can be accessed. Further, the user interface can provide alerts regarding the reasons for the patient's visit, and can include messages from staff that can be programmed to self-delete and not become a permanent part of the medical record.

Some embodiments of the invention provide a user interface that can function as an epicenter for physician care allowing medical synthesis of the problems confronting the patient. To make the best decisions, the physician needs to understand the entire picture of a patient's life, while being able to hone in on any detail. Some embodiments of the invention can function as an EMR similar to how a ganglion cell is to the brain or the spinal cord to the body. Some embodiments of the invention provide the ability for the findings of a doctor "today's visit" to be rapidly entered into the relevant fields/tabs/screens within an EMR, streamlining data entry required for documentation and interpretation. Some embodiments of the invention provide can provide a starting point for caring for a patient, where new orders can be placed or messages can be sent. Using a summary review table, the physician can navigate and interact with the entire EMR for the patient without the need to scroll through multiple screens, and can be interoperable to enable extraction of pertinent information from other sources.

Medical sub-specialization, information overload, and increased complexity of reimbursements for service all conspire to remove the doctor from caring for a patient. Some embodiments of the invention provide can save the physician time that can be used for time with the patient rather than time used with a computer screen and a mouse. Finally, there is the new tool that makes the computer age successfully replace the paper age in properly caring for patients. Some embodiments of the invention provide can allow the doctor and hospitals to comply with insurance companies and the government which demand that they comply and be responsible for their billing. Some embodiments of the invention provide can help transform the mindset of a doctor from being a medical provider without any knowledge of business or finance, to a doctor able to participate in revenue cycle management. Some embodiments of the invention provide can, therefore, insert the doctor back into being the quarterback of the healthcare system. Some embodiments of the invention provide can give the physician the time to be a healer while at the same time rapidly synthesizing information that can cut costs and improve outcome quality. In an ever-expanding interoperable complex world, some embodiments of the invention provide can function as a doctors Genie and magic carpet that seamlessly transports the physician though the maze of data entry and provides the overview needed for medical synthesis.

Some computerized or electronic medical record ("EMR") systems provide computerized interface between medical professionals and staff and one or more medical records databases. Some embodiments of the invention disclosed herein include a medical service tracking server system and method that can be linked to or otherwise accessed from a conventional EMR system. Some non-limiting examples of such conventional EMR systems include the MD Office medical records and practice management systems distributed by MD Office, Inc. USA, 1967 Oak Tree Road, Edison, N.J., 08820, USA. In some other embodiments, any conventional EMR system can be coupled or linked with the medical service tracking server system and method described herein.

Some embodiments of the invention include a medical service tracking server system and method that can be included as an add-on software package to a conventional medical record system such as the aforementioned MD Office medical records system. In some embodiments, tasks associated with an add-on software program can be seamlessly linked and/or incorporated into one or more core software tasks or modules of the conventional medical record system such as MD Office. In some embodiments, application programming interfaces (hereinafter "APIs") can be used to connect and transmit data between one or more software modules of the medical service tracking server system and method, and one or more conventional medical records system such as MD Office and/or one or more patient records and/or databases comprising patient records. For example, in some embodiments of the invention, the medical services tracking server system and method can be configured to receive patient data from a master patient index or a medical provider. In some further embodiments, the medical services tracking server system and method can auto-populate various data fields (including information fields, tables, or windows) from a variety of sources. The sources can include electronic, physical (paper records), and human input. In some embodiments, and electronic dataflow can be established between the medical services tracking server system and method and one or more computer systems of servers that comprise patient information (e.g., such as electronic medical records). In some embodiments, the dataflow comprises a one-way flow from the source to the medical services tracking server system and method. In some other embodiments, the dataflow comprises a two-way flow from the source to the medical services tracking server system and method, and from the medical services tracking server system and method to the source. This information can be any medical diagnosis information prepared by a medical practitioner, any medical procedures or services provided to the patient, including procedures or services by claims made, or billings or payments including billing signed off by a physician as detailed above, billings, payments, or other information from anywhere in the EMR chart treatment summaries, and/or diagnosis summaries, and/or patient feedback summaries, and/or other physician summaries, patient outcome summaries, treatment summaries, and/or diagnosis summaries, and/or patient feedback summaries, and/or other physician summaries or treatments, and so on. For example, in some embodiments, the medical service tracking server system and method discussed below can display and/or auto-populate with at least one of a patient's prior medical procedures, diagnostic tests, surgeries, current medications, current illnesses, treated illnesses, and so on.

In some further embodiments, new software features of the medical service tracking server system and method can be added to an existing application such as MD Office without modifying the existing code of the application. In some other embodiments, the medical service tracking server system and method can function as an independent application, not linked, overlaid, or otherwise interfaced with any conventional medical record system such as MD Office.

Figure 2:
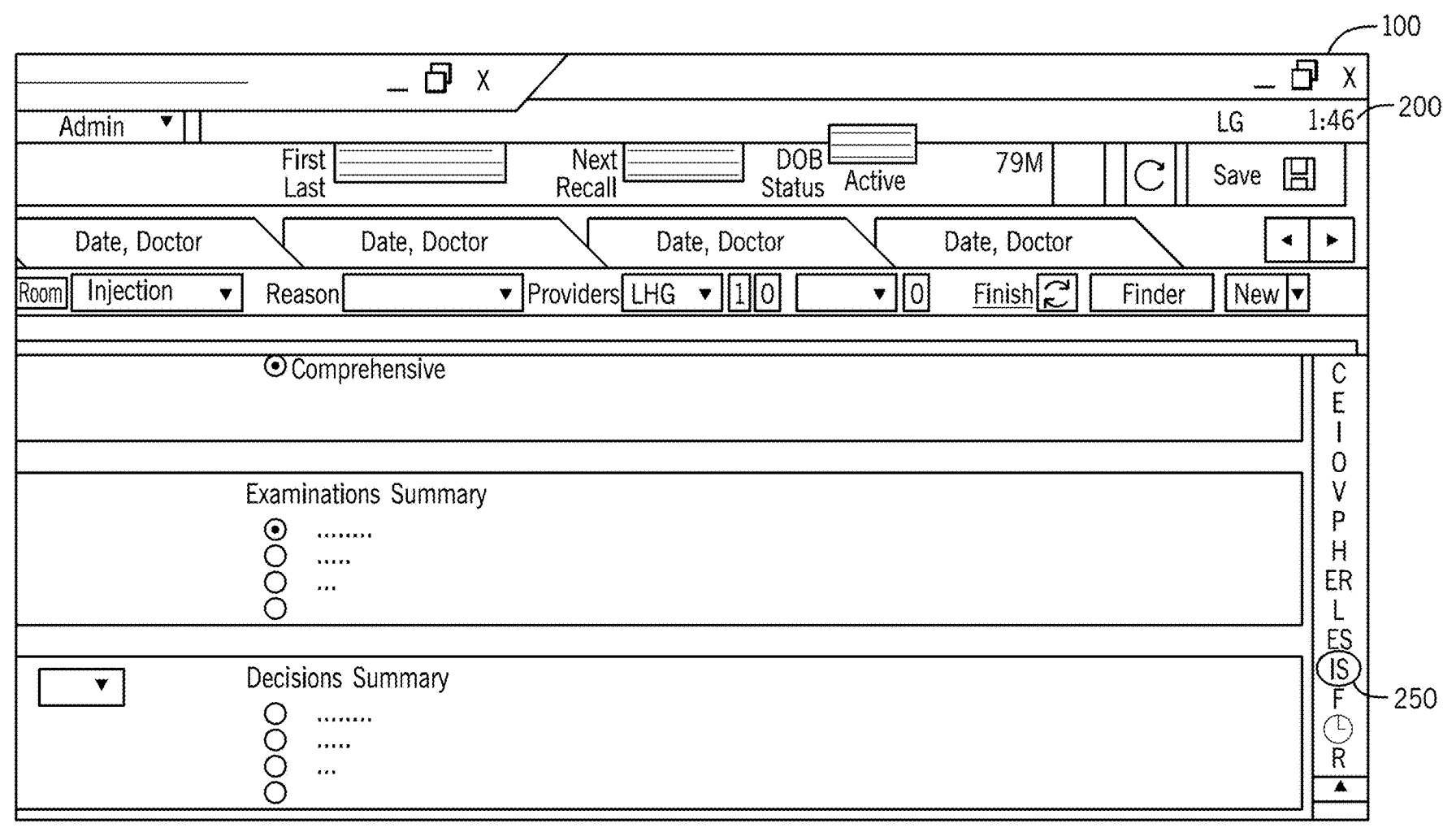

FIG. 1 illustrates sample medical record system 100 useful for deploying or launching embodiments of the invention described herein. In some embodiments, a user, such a medical practitioner, can utilize a conventional medical record system such as MD Office or another medical record system to launch or enter a medical services tracking system that can display information dashboards, tables, charts, windows, as tailored by a user. FIG. 2 illustrates a medical record window 200 of the medical record system 100 useful for deploying or launching embodiments of the invention described herein. In some embodiments, the medical record window 200 of a conventional medical record system can include a medical tracking system launch icon 250 to facilitate access to and/or launch of one or more embodiments of the medical service tracking system and method.

In some embodiments, a user can use the medical tracking server system launch icon 250 or other displayed icon or display element to exit the medical record server system 100 with the intent of accessing or launching the medical service tracking server system and method described herein. In some further embodiments, the launch icon 250 can be used to temporarily halt the medical record system 100 and access or launch the medical service tracking server system and method. In some other embodiments, the launch icon 250 can be used to access or launch the medical service tracking server system and method while the medical record system 100 continues to run in parallel, continues to run in a background mode, and/or is switched to an idle mode.

Figure 3:
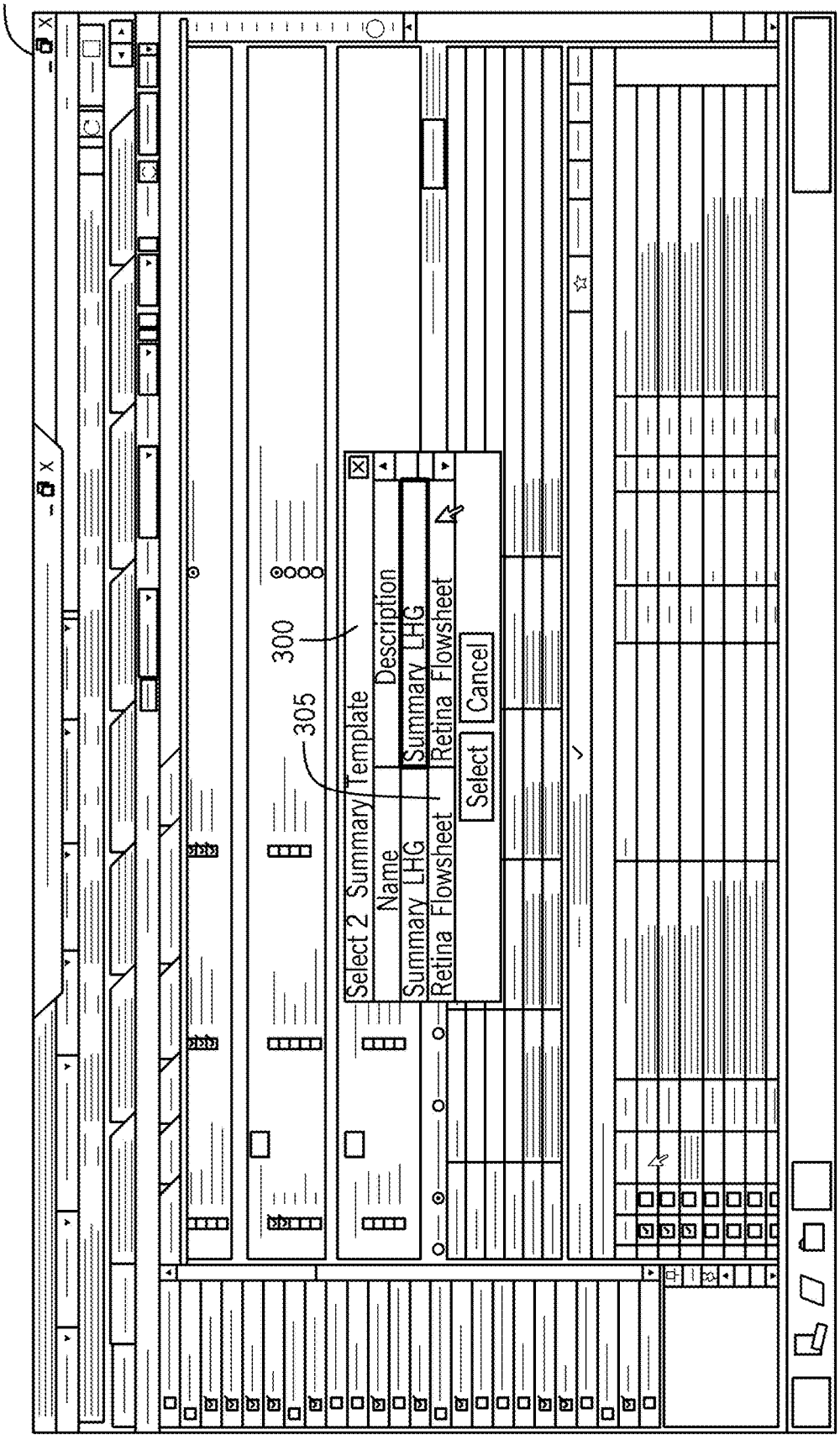
FIG. 3 illustrates a medical record dashboard selection window useful for selecting and launching embodiments of the invention described herein.

Referring to FIG. 3, illustrating a medical record dashboard selection window useful for selecting and launching embodiments of the invention described herein, in some embodiments, after a user selects or clicks the launch icon 250, a medical record dashboard selection window 300 can be displayed. The medical record dashboard selection window 300 can include one or more selectable medical record dashboards from which a user can select to access at least one medical record dashboard. For example, in one non-limiting example embodiment, the user can select "Retina Flowsheet" 305 to access and/or launch a medical record dashboard including a retina flowsheet. In some further embodiments, the at least one medical record dashboard can include any number of selectable medical records for any medical condition, and/or any medical diagnosis, and/or any medical treatment.

Some embodiments of the invention comprise one or more displayed tables and/or dashboards that function as a medical or physician command center. The command center can enable a user to work with a single display that can be configured as a central medical record entry, access, update, recording, and archival site. For example, FIG. 4A illustrates a medical record dashboard 400 in accordance with some embodiments of the invention. In some embodiments, the medical record dashboard 400 can be displayed by the user following the user's selection of at least one medical record dashboard from the medical record dashboard selection window 300. In some embodiments, the medical record dashboard 400 can display data from one or more medical records, and/or track medical procedures and services based on claims made or billing signed off by a physician for one or more delivered medical procedures or services. Some embodiments of the invention include a medical service tracking server system and method that can dynamically link to various external databases comprising patient information that can be displayed in the medical record dashboard 400. For example, in some embodiments, the medical service tracking server system and method can function as a portal to patient information prepared by the user or patient information from other sources. Further, in some embodiments of the invention, the medical record dashboard 400 can be auto-populated as a function of claims made or billing signed off by a physician. In this instance, any data displayed within the medical record dashboard 400 is derived from one or more claim records that have been billed for one or more procedures or services have previously been provided to the patient. In some other embodiments, auto-population can be enabled in both directions interacting as a switchboard between the entire EMR and the medical record dashboard 400 along with what is added to any window, sub-window, column or entry in the medical record dashboard 400 being automatically added to the appropriate part of the chart for documentation.

In some embodiments, the medical record dashboard 400 can display information related to any medical procedures or services in relation care of a patient. For example, in some embodiments, the medical record dashboard 400 can display information related to medical procedures or services in relation to retinal eye medical care of a patient. In some embodiments, the medical record dashboard 400 can display information including components where there is a summary of the patient's problem list that a user can input patient information and constantly update and change. Further, this information can be auto-populated with the touch of a button into a designated location such as the current plan documenting the patient's current visit (thus aiding documentation for the current visit). Further, whatever is important for a user to input into the day's visits for documentation can be initially inputted in the table, and then permanently into the day's patient visits. Further, the summary section of the medical record dashboard 400 can be constantly fluid, and can be changed at every visit rather than being written to an unchangeable document or file (e.g., such as a PDF). Further, any patient data that is inputted, received, analyzed, or created can be auto-populated into any portion of the dashboard 400, and/or can form a dataflow out of the medical record dashboard 400 to another electronic system or server, or another user, observer, or other $3^{rd}$ party.

In some embodiments, the medical record dashboard 400 can display various windows and sub-windows based on a user preference and/or current or previous user interaction with the medical record dashboard 400. For example, in some embodiments, the medical record dashboard 400 can display a problems window 425 and/or a surgeries window 450 where information related to a patient's medical problems and surgeries can be displayed in information columns 600, 700 respectively. Further, in some embodiments, patient information related to allergies and drugs can be displayed within the allergies/drug section 460. This information can be auto-populated from a variety of sources, or inputted by a user.

In some embodiments, the medical record dashboard 400 can include a summary window 475 enabling a user to view and edit summary information related to the patient, any details of care provided to the patient, and/or and any medical diagnosis information prepared by a medical practitioner. Further, in some embodiments, the medical record dashboard 400 can also display detailed information related to any medical procedures or services provided to the patient, including procedures or services that are auto-populated by claims made, or billings or payments including billing signed off by a physician as detailed above. For example, in some embodiments, the medical record dashboard 400 can display a medical tracking display window 500 including information columns 800 that can be auto-populated by claims made or billings signed off by a physician. The auto-population can include billings, payments, or other information from anywhere in the EMR chart. For example in some embodiments, the information that is auto-populated can include treatment summaries, and/or diagnosis summaries, and/or patient feedback summaries, and/or other physician summaries, and so on. For example, in some embodiments, the medical service tracking server system and method can display and/or auto-populate at least one field, table, or window with at least one of a patient's prior medical procedures, diagnostic tests, surgeries, current medications, current illnesses, treated illnesses, and so on. The medical services tracking server system and method can auto-populate various data fields via an electronic dataflow established between the medical services tracking server system and method and one or more computer systems of servers that comprise patient information (e.g., such as electronic medical records). The dataflow can comprise a two-way flow from the source of patient data to the medical services tracking server system and method, and from the medical services tracking server system and method to the source. In some embodiments of the invention, this information can be any medical diagnosis information, any medical procedures or services provided to the patient, procedures or services by claims made, or billings or payments including billing signed off by a physician as detailed earlier, any information from anywhere in the EMR chart including treatment summaries, and/or diagnosis summaries, the patient's prior medical procedures, diagnostic tests, surgeries, current medications, current illnesses, treated illnesses, and/or patient feedback summaries, and/or other physician summaries, patient outcome summaries, treatment summaries, and/or diagnosis summaries, and/or patient feedback summaries, and/or other physician summaries or treatments. Further, in some embodiments, the information that is auto-populated can include patient outcome summaries. For example, in some embodiments, the medical service tracking server system and method process a plurality of patient outcomes and display an analysis of patient outcomes based at least in part on patient information from treatment summaries, and/or diagnosis summaries, and/or patient feedback summaries, and/or other physician summaries or treatments. In some embodiments, the patient outcomes can include or comprise physician quality reporting system (PQRS) quality measures. In some embodiments, calculated or reported patient outcomes can include or comprise at least one PQRS measures code.

The medical record dashboard 400 can include miscellaneous information identifying the patient, information related to the patient's insurance plan, physicians and referring physicians, and the patient's current balance. Other information can relate to the patient's prior visit, prior diagnosis or procedure and any important information relevant to the next visit. Additional information can relate to the current visit, including history of illness and chief or current medical complaint, billing information, and retrievable medical information including pharmacy information. For example, in some embodiments, the medical record dashboard 400 can include a patient insurance entry 401, referring doctor entry 402, and primary care physician entry 403. The medical record dashboard 400 can also include patient balance entry 404, and a high deductible plan entry 405. Important patient information related to a pending or current visit can include a "days left post op period" entry 406 and/or an information alert 465. In some embodiments, the information alert 465 can be auto-populated based on other information or entries in the medical record dashboard

400. In other embodiments, the information alert 465 can be set by any user to alert the user or other user of information relevant to the patient. In some embodiments, the information alert 465 can comprise a daily technician update, including information to medical information such as blood pressure, or whether the patient is pregnant, or any other urgent information with which a member of a health care team can alert another member. Further, this information can become permanent or can be deleted from the dashboard 400, and from any record or table accessible from the dashboard 400, including any medical record. Further, this information can serve as or be configured as a "sticky note" that can be removed from any of the above-mentioned records. For example, the "sticky note" can be an electronic sticky note riding on the dashboard or any record accessible from the dashboard, or a physical sticky note attached to a physical record, chart or table. Further, the dashboard 400 can provide improvement as described where test interpretations and evaluation of patients, once documented and billed, usually become date stamped, and cannot be easily amended without applying a new date of amendment. In some embodiments, the medical service tracking server system and method can improve and follow care that not necessarily be used as part of a particular days medical record. Therefore, months or years apart, physicians can add notes into the table when new findings, discoveries, or realizations warrant it without feeling encumbered that they are "changing past medical record" and a disclosure of such can be at the bottom of the dashboard 400. Allowing physicians and technicians to add and change notes within this dashboard 400 (rather than changing the patients EMR chart) can enable them to summarize critically important health/history/treatment data, which can then be used as a quicker point of reference while examining the patient. Notes that sit on the table can flag or alert the physician to an important medical change, and can be used as an additional form of communication to strengthen lines of communication between technicians/clinic staff and physicians to better ensure that the physician is quickly directed to important medical information.

In some other embodiments, a daily technician update can be accessed or otherwise made visible to the user in at least one other portion of the dashboard 400. In some embodiments, the information alert 465 can be displayed in a specific color and/or with a specific graphic and/or animation. For example, in some embodiments, the information alert 465 can comprise a flashing red animation. To protect the physician during an audit, a statement on the dashboard 400 can be added that "notes on this table" are not necessarily added at the time listed as the date and not for documentation in a medical record, but as a medical reference tool.

Some embodiments include an alert or access to one or more letters or results from outside (icon 407) systems or third parties. Some further embodiments include an alert or access to letters sent 408. The letters can be written, typed, and/or one or more dictated letters from the user and/or another medical provider. Some embodiments include an entry or access to the current day's history, the current day's plan, and/or to the current day's billing. For example, some embodiments include a "Today's history" button or icon 409, a "Today's plan" button or icon 411, and a "Todays billing" button or icon 413. In some further embodiments, a correspondence button or icon 436 can be used to view, access, enter, and/or auto-populate correspondence related to a patient's care. This can include any medical record and/or any correspondence generated while the patient is under care by the user and/or any other physician or medical practitioner, medical services provider, and/or medical insurance company.

In some embodiments, the medical record dashboard 400 can display a summary of the patient's problem list that a user can input patient information and constantly update and change. For example, some embodiments include the ability to enter or access current complaints of the patient (button 430). In some embodiments, a user can add or update one or more entries of the patient's chief or current complaints, and/or a user can view one or more entries of the patient's chief or current complaints using the button 430. In some embodiments, if a user activates (e.g., by clicking using a cursor) the button 430, information related to the patient's current medical problems or complaints can be shown and/or displayed and/or updated by any user or user's assistant. In some embodiments, the information can be auto-populated into the medical record dashboard 400 and/or to any other accessible window displayed by the medical services tracking server system and method.

In some embodiments, the medical record dashboard 400 can display a today's examination access button 432 that a user can use to view and/or input patient information, patient examination results, tests, notes, or any information relevant to the medical care of the patient. In some embodiments, a user can add or update one or more entries of the today's examination, and/or a user can view one or more entries of the examination. In some embodiments, if a user activates (e.g., by clicking using a cursor) the button 432, information related to the patient's examination including medical problems or complaints patient information, patient examination results, tests, notes, etc., can be shown and/or displayed and/or updated by any user or user's assistant. In some embodiments, the information can be auto-populated into the medical record dashboard 400 and/or to any other accessible window displayed by the medical services tracking server system and method. In some embodiments, any stored or displayed patient's examination can be cleared from the medical record dashboard 400 following some time period once the patient visit is complete. In some embodiments, the medical record dashboard 400 can remove display or access to a previous patient's examination details once the patient visit has ended. In some other embodiments, the medical record dashboard 400 can remove display or access to a previous patient's examination details later in the day of the patient's visit, or before the following day, or at any time selectable by the user or user's assistant. In some embodiments, the information can be auto-populated into the medical record dashboard 400 and/or to any other accessible window displayed by the medical services tracking server system and method. In some embodiments, the information can be auto-populated into any EMR system for recordation into one or more EMR's of the patient. In some embodiments of the invention, for any auto-populated information that includes technical information without any associated professional interpretation, the medical services tracking server system and method can provide a visual and/or audible alert to enable a user to provide an update for auto-population to an EMR system.

In some embodiments, the medical record dashboard 400 can also include at least one link to information from external databases, providers, hospitals (e.g., such as a discharge summary), clinics and/or testing laboratories, etc., (e.g., where the information can include the overall diagnostic imaging center of the practice for certain pieces of equipment and into the machine to actually see all of the study). In the latter example, the medical record dashboard 400 can receive information from at least one database and/or server and/or controller coupled to receive data from the diagnostic equipment. Further, some embodiments include an entry or access to the National Patient Registry or other kind of registry (link 415), hospital EMR (link 417), imaging center 419 (including accessing software imaging and diagnostic management systems to handle many diagnostic images and studies or specific diagnostic equipment), and Eprescribe link 421.

In some embodiments, the user can access at least one Eprescribe database, server, and/or website directly from the dashboard 400 using the Eprescribe link 421. Further, in some embodiments, orders can be auto-populated into the plan or order screen of EMR ("Orders" link 423). For example, in some embodiments, during or after completion of a patient examination, any medical service, medical test or diagnostic, or other medical service can be auto-populated into an order section of the chart. In some embodiments, any recommendation for a return visit can be viewed, accessed, and/or auto-populated using the return visit button or icon 434. For example, in some embodiments, the recommendations can be any advised next steps in the patient's care, any diagnosis, prescriptions, tests, etc. In some embodiments, the aforementioned "Today's plan" button or icon 411 can be used to view, access, and/or auto-populate details and systems including for a day's activities for the patient examination.

In some embodiments, a single button or icon entitled "clinical research study diagnostic equipment" (button 424a) can take a user (e.g., a physician) instantly or immediately to the piece or pieces of equipment that were used that or another day for testing so the physician can now measure and enter the findings. This can be internal in the user's practice so that any diagnostic equipment can be accessed. In some embodiments, the same or another button can provide a link in the major table to an image or diagnostic management software system. In this way, some embodiments can handle the tremendous amount of diagnostic equipment and images, and unlike prior art tables that just provide access to a PDF, these embodiments provide access to not just one single piece of diagnostic equipment but all of them and the complete study, not just a "slice", can be evaluated and comparison of changes over time made.

Once entered, the data can be auto-populated into the dashboard 400 (e.g., such as a retina flowsheet) under other column 1200, where each clinical research study would have other factors followed such as central macular thickness ("CMT"), or ischemic index ("ISI"). Further, the second button (button 424b) can take the user to either the company sponsoring the clinical research website (sometimes a pharmaceutical company and other times a company that invented a device). The clinical researcher could immediately go to this website and input any data that was obtained from that visit from the diagnostic equipment button 424a, and/or to a research spreadsheet where the user (e.g., a clinical researcher in this example embodiments) can input the data, or where the data can be auto-populated (e.g., from the other column 1200 or into the other column 1200).

Figure 4C:
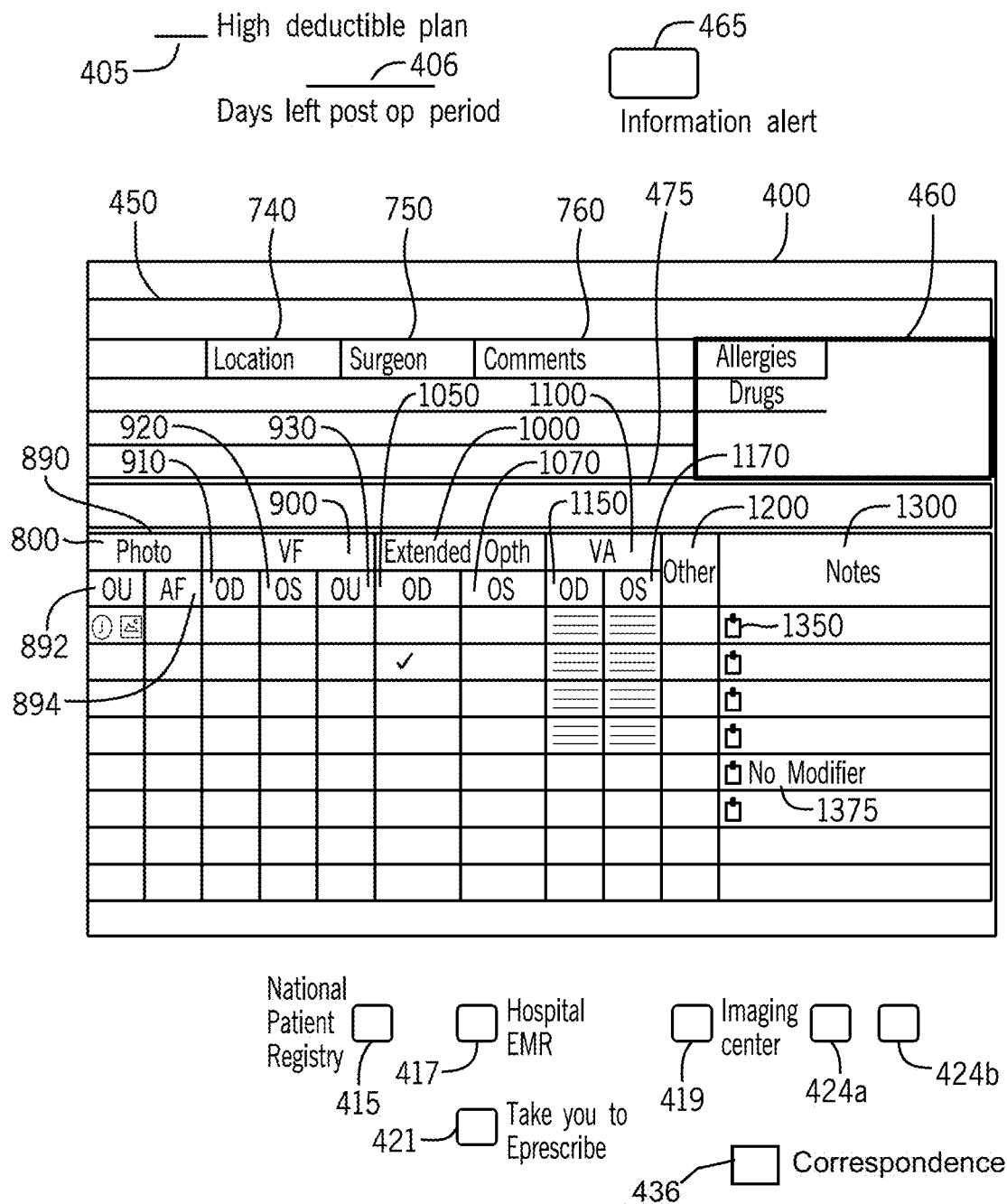
FIG. 4C illustrates a portion of the medical record dashboard of FIG. 4A in accordance with some embodiments of the invention.
Figure 4D:
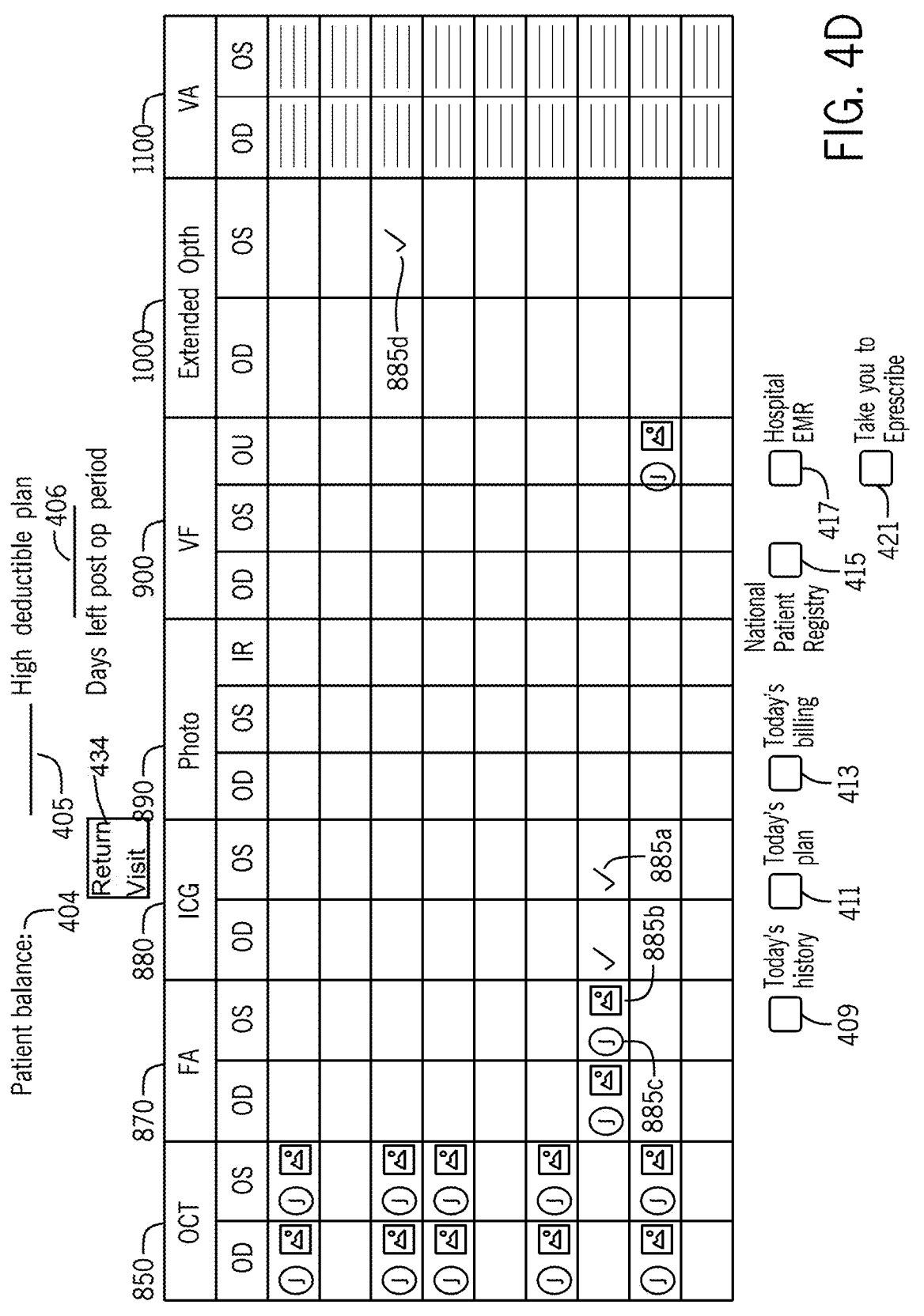

Further details of the problems window 425, surgeries window 450, and medical tracking display window 500 and are provided in FIGS. 4B-4D illustrating enlarged views of portions of the medical record dashboard 400. For example, FIG. 4B illustrates a portion of the medical record dashboard of FIG. 4A in accordance with some embodiments of the invention. As illustrated, in some embodiments, the information columns 600 of the problems window 425 can include a date and time information in entered date column 610, a timeline column 620, an "ICD" column 630 for international classification of disease codes including international classification of disease codes version 9 or version 10 (hereinafter collectively referred to as "ICD code") information, location of the problem or disorder (shown as "OD", "OS", "OU" identifying right eye, left eye, both eyes), or from any part of the body, and a diagnosis column 650 for detailing information related to an initial diagnosis or final diagnosis of a patients problem or disorder that can be auto-populated or inputted. Further, in some embodiments, the information columns 700 of the surgeries window 450 can include information related to services or procedures that were provided to the patient (procedure columns 720), a description of the services or procedures performed (description columns 730), and when the services or procedures were provided (timeline columns 710). Referring to FIG. 4C, in some embodiments of the invention, the surgeries window 450 can include location information 740, surgeon or doctor information 750, and a comments section 760.

Referring to the medical tracking display window 500, the information columns 800 can include a date column 805, and a procedure column 810 illustrating or providing access to information detailing one or more procedures performed on the patient. Further, the procedure column 810 can include an "OD" column 815, and "OS" column 820 providing right and left eye procedure information, or could be a body part (i.e., orthopedic surgery limb versus spine). In some embodiments, information related to the medical provider, the location where the procedure was performed, and office visit information can be provided to the user in the provider column 830, and unit column 840, and office visit column 845.

In some embodiments of the invention, the user can view information related to tests and procedures performed on the patient. For example, in some embodiments, these can include information related to one or more medical imaging procedures such as an optical coherence tomography ("OCT"), or fluorescein angiography ("FA"), and/or indocyanine green chorioangiography ("ICG"), or any current procedural terminology code (hereinafter "CPT code"), including any CPT code found in the American Medical Association CPT 2015 professional edition, the entire contents of which is incorporated by reference. Moreover, the user can view information related to tests and procedures performed on the patient based on an ICD code.

In some embodiments, medical procedures performed (including any of the aforementioned medical imaging procedures) that have been billed and claimed can be viewed or accessed by a user within any of the "OCT" column 850 (split as an "OD" column 855 and "OS" column 860), an "FA" column 870 (split as an "OD" column 872 and "OS" column 874), and/or "ICG" column 880 (split as "OD" column 882 and "OS" column 884).

Referring to FIG. 4C, illustrating a portion of the medical record dashboard of FIG. 4A in accordance with some embodiments of the invention, the information columns 800 can include a photo column 890 configured to enable a user to access any photographic images of the patients eyes including optical and auto-fluorescent images of the eyes ("OU" column 892 and "AF" column 894). In some embodiments, if visual function tests were performed, information can be viewed or accessed in the "VF" column 900 (including an "OD" column 910, "OS" column 920, and/or "OU" column 930). Some embodiments also include an extended ophthalmology column 1000 (including "OD" column 1050 and "OS" column 1070), and a visual acuity column ("VA"

column 1100, including "OD" column 1150, and "OS" column 1170). In some embodiments, as described earlier, other details of various tests, procedures or services can be viewed or accessed in the other column 1200. Further, information associated with any of the user-accessible tests, procedures or services or other notes provided by the user and/or medical provider can be viewed or accessed in the notes column 1300 using one or more notes access icon 1350 and/or by viewing a note entry 1375 (e.g., and/or any note entered using the note entry window 1305). The information can also be auto-populated into the EMR plan pages. The medical services tracking server system and method can auto-populate various data fields of the medical record dashboard of FIG. 4A via an electronic dataflow established between the medical services tracking server system and method and one or more computer systems of servers that comprise patient information (e.g., such as electronic medical records). The dataflow to and from the medical record dashboard of FIG. 4A can comprise a two-way flow from the source of patient data to the medical services tracking server system and method, and from the medical services tracking server system and method to the source.

Some embodiments of the invention include visual cues, icons, or markers representing and/or enabling access to detailed information related to medical services, procedures or tests provided to the patient. Further, by employing data visualization techniques to train the user's eye to quickly identify these icons or makers can increase the efficiency of user accessing key medical indicators such as test results and surgical histories. For example, in some embodiments, medical services, procedures or tests performed or provided can be assigned a visual code, icon, or graphical marker. For example, FIG. 4B at least shows visual cues, icons, or markers 885 representing medical services, procedures or tests performed or provided to the patient. In some embodiments, the information columns 800 within the medical tracking display window 500 can include at least one "test done, no image attached" icon 885*a*, one or more "see image in order viewer" icon 885*b*, at least one "view order interpretation" icon 885*c*, and/or at least one "procedure billed or claims made" icon 885*d*, where an appearance in the medical record dashboard 400 represents a claim was made, and a change in color or other method (italics, bold, etc. can represent whether the bill was paid. Further, FIG. 4D illustrates another portion of the medical record dashboard 400 of FIG. 4A in accordance with some embodiments of the invention and shows example of "test done, no image attached" icon 885*a*, "see image in order viewer" icon 885*b*, "view order interpretation" icon 885*c*, and "procedure billed or claims made" icon 885*d*, where an appearance in the medical record dashboard 400 represents a claim was made, and a change in color or other notification method can represent whether the bill was paid. Data visualization icons and makers housed in the table can be used to quickly identify billing or coding errors, and thus can empower the physician to be proactive and thorough in areas of compliance. The use of these icons to identify potential errors in compliance can provide an additional level of protection and proofing to reduce and prevent potential compliance and/or malpractice errors.

In some embodiments of the invention, the medical record dashboard 400 can provide a text summary of any aspect of the medical record dashboard 400. As described earlier, the summary window 475 can enable a user to view and edit summary information related to the patient, any details of care provided to the patient, and/or and any medical diagnosis information prepared by a medical practitioner. In some embodiments, the user can add and/or edit the summary information. For example, FIG. 5A depicts a medical summary update process in accordance with some embodiments of the invention. In some embodiments, the medical record dashboard 400 including the problems window 425, surgeries window 450, summary window 475, and medical tracking display window 500 can include summary comments 482 that can be entered, updated, expanded using the summary input window 484. In some embodiments, a user can enter information within the summary input window 484 for entry into the summary window 475.

Figure 5B:
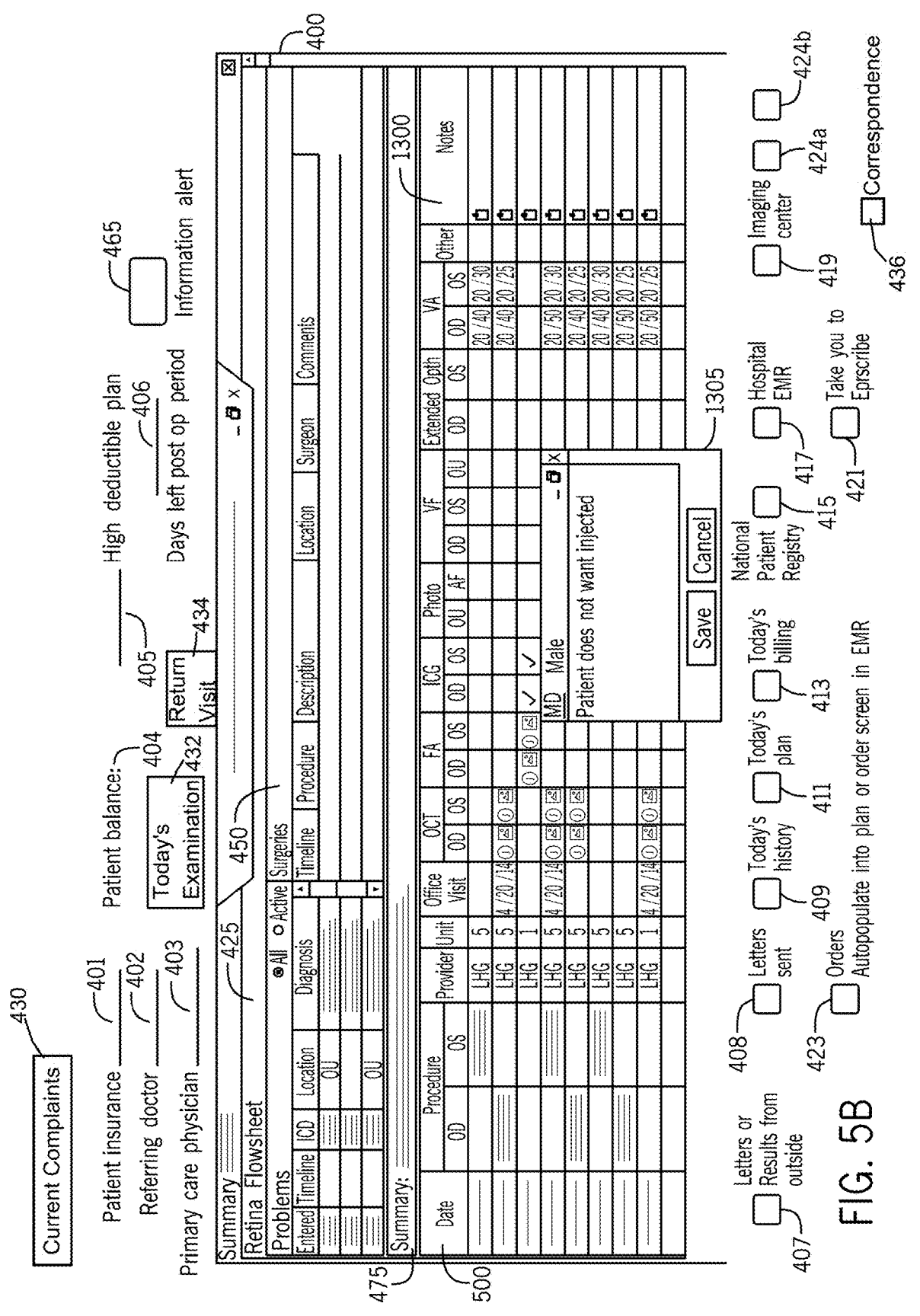

In some embodiments of the invention, the user can add or update information associated with any of the user-accessible tests, procedures or services or other notes provided by the user and/or medical provider in the notes column 1300. For example, FIG. 5B illustrates a notes update process in accordance with some embodiments of the invention. In some embodiments, the medical record dashboard 400 comprising the problems window 425, surgeries window 450, summary window 475, and the medical tracking display window 500 with notes column 1300 can be updated with one or more notes using the note entry window 1305. In some embodiments, placement or viewing functions can be toggled using a left or right mouse click function. For example, in some embodiments, following an initial impression or diagnosis, a right click can be updated or shown in a note (e.g., through note entry window 1305), and/or a left click can show in the summary (e.g., summary window 475 as summary comments 482). Further, a right-click for instance or other method can insert what is typed in the table into the corresponding area of the medical chart (e.g., the plan), whereas a left click would insert only into the table and not any other location within the EMR.

Figure 6:
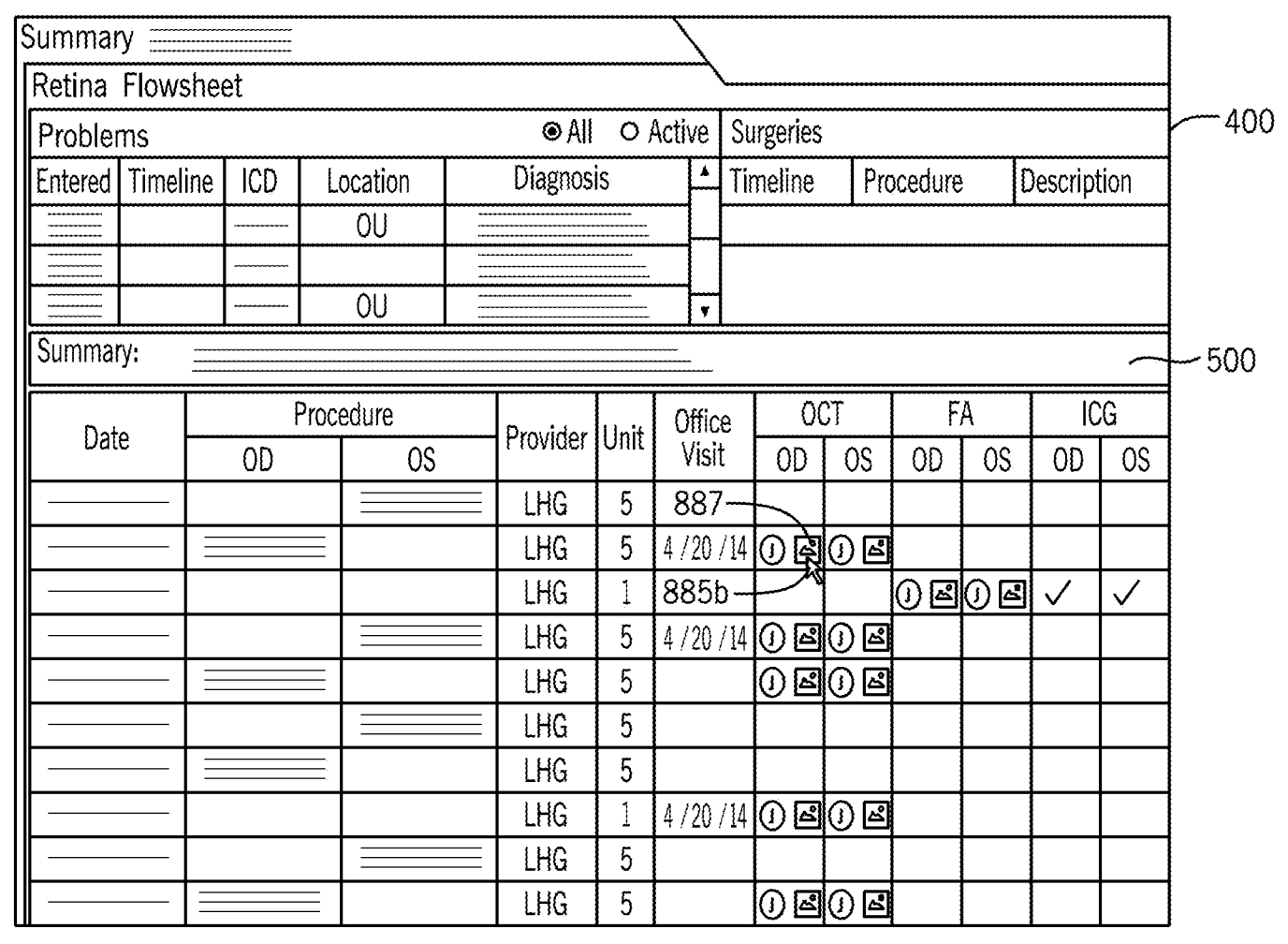

Regarding the visual cues, icons, or markers 885 (referred to above and shown at least in FIG. 4B), in some embodiments, a user can access underlying information linked to the visual cues, icons, or markers 885. For example, using a single click or mouse-over, a user can use the medical tracking display window 500 of the medical record dashboard 400 to access and view any information auto-populated within the medical tracking display window 500 and/or other windows or sub-windows of the medical record dashboard 400. For example, FIG. 6 illustrates a user action record access process in accordance with some embodiments of the invention. In some embodiments, a user action 887 (depicting a user click or mouse-over of a cursor) can enable a user to access and view information (in this example, information lined to "see image in order viewer" icon 885*b*). In some further embodiments, a user can use a single click or mouse-over to user can access and view any information within any portion of the medical record dashboard 400. Further, in some embodiments, a user can use left and right mouse clicks to navigate from one portion of the medical record dashboard 400 to another. Furthermore, in some embodiments, a right-click mouse function update the user and/or display any important information in the medical record dashboard 400, and a left-click can bring the user back to another portion of the medical record dashboard 400.

Figure 7:
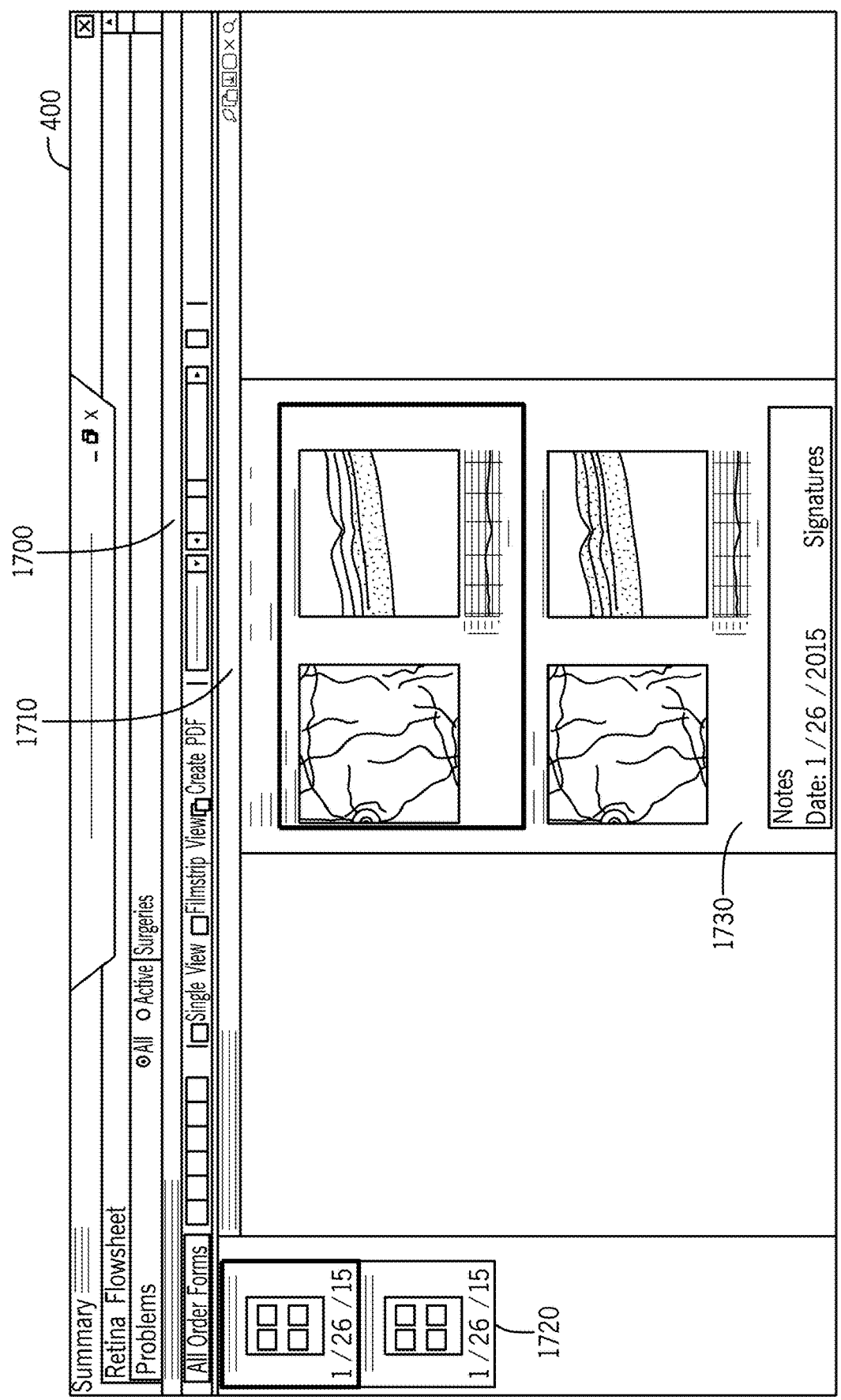
FIG. 7 illustrates a medical records access window in accordance with some embodiments of the invention.

As an example embodiment of the invention, the medical service tracking server system and method can display at least one medical record as a result of the user action 887. For example, FIG. 7 illustrates a medical records access window 1700 in accordance with some embodiments of the invention. In some embodiments, the user's action (represented by user action 887) can direct the medical service tracking server system and method to display the medical record access window 1700 including a medical record display 1710. Further, in some embodiments, at least one medical record 1730 can be selected from the medical record list 1720 for viewing in the medical record display 1710. As illustrated in FIG. 7, in some embodiments of the invention, the at least one medical record 1730 can include an image or photograph such as an optical and/or fluorescein angiogram image. In other embodiments, the at least one medical record 1730 can comprise an X-ray image. In some further embodiments, the at least one medical record 1730 can include an MRI scan or any report or anything ordered or performed by the physicians. In some embodiments, the at least one medical record 1730 can comprise one or more dictated letters from the user or another medical provider. Further, in some embodiments, the at least one medical record 1730 can comprise a record or any portion of a correspondence from another medical provider.

In some embodiments of the invention, the medical service tracking server system and method can enable a user to access underlying information linked or related to diagnostic codes. In some other embodiments, the medical service tracking server system and method can enable a user to access underlying information linked or related billing codes. For example, in some embodiments, using a single click or mouse-over, a user can use the medical tracking display window 500 of the medical record dashboard 400 to access and view any information related to diagnostic and/or billing codes. In some embodiments, the diagnostic and/or billing code information and payment history can be displayed in a separate document or window. In some other embodiments, diagnostic and/or billing code information can be display overlaid onto the medical record dashboard 400 (e.g., as a pop-up window or transient text and/or graphics).

In some embodiments, the at least one medical record 1730 can comprise a transition of care document (hereinafter "CCD"). In some embodiments of the invention, the medical services tracking server system and method can be configured to receive one or more CCDs from one or more medical providers for display to the user. In some embodiments, medical services tracking server system and method can be configured to extract information from the CCD for display to the user. For example, in some embodiments, information from a received CCD can be extracted and used to populate one or more data columns or fields of the medical record dashboard 400 and/or one or more linked data columns or fields of the medical record dashboard 400. In some other embodiments, the medical services tracking server system and method, enabled by the system 30, can be configured to receive direct messaging information. The medical services tracking server system and method can be configured with standards and profiles required for interoperability and document-based health information exchange with other healthcare organizations. These can include IHE profiles, CDA and CCD, NwHIN Direct, HL7v2, HL7v3, DICOM, X12, ITK (UK), DMP (France), and NEHTA (Australia), etc. For example, in some embodiments, the system 30 can include an HL7 message router and schemas for exchange of direct messages including a graphical editor for transforming messages and data.

In some embodiments of the invention, the user can retrieve and/or update information related to a medical diagnosis. For example, FIG. 8 illustrates a medical record and diagnosis update process in accordance with some embodiments of the invention. In some embodiments, the medical record dashboard 400 including problems window 425, surgeries window 450, summary window 475, and medical tracking display window 500 can include an option to enable a user to update or enter at least one medical diagnosis using a medical record/diagnosis window 1750. In some embodiments, multiple medical diagnoses can be provided or updated by a user. In some embodiments, the user providing the medical diagnosis can be any medical practitioner providing the service or procedure to the patient. In some other embodiments, the medical record/diagnosis window 1750 can be updated by a user other than the medical practitioner providing the service or procedure to the patient.

Further, in some embodiments, information can also be auto-populated into the EMR plan pages. The medical services tracking server system and method can auto-populate various data fields related to information in any one of the problems window 425, surgeries window 450, summary window 475, and record/diagnosis window 1750 via an electronic dataflow established between the medical services tracking server system and method and one or more computer systems of servers that comprise patient information (e.g., such as electronic medical records). The dataflow can comprise a two-way flow from the source of patient data to the medical services tracking server system and method, and from the medical services tracking server system and method to the source.

Figure 9:
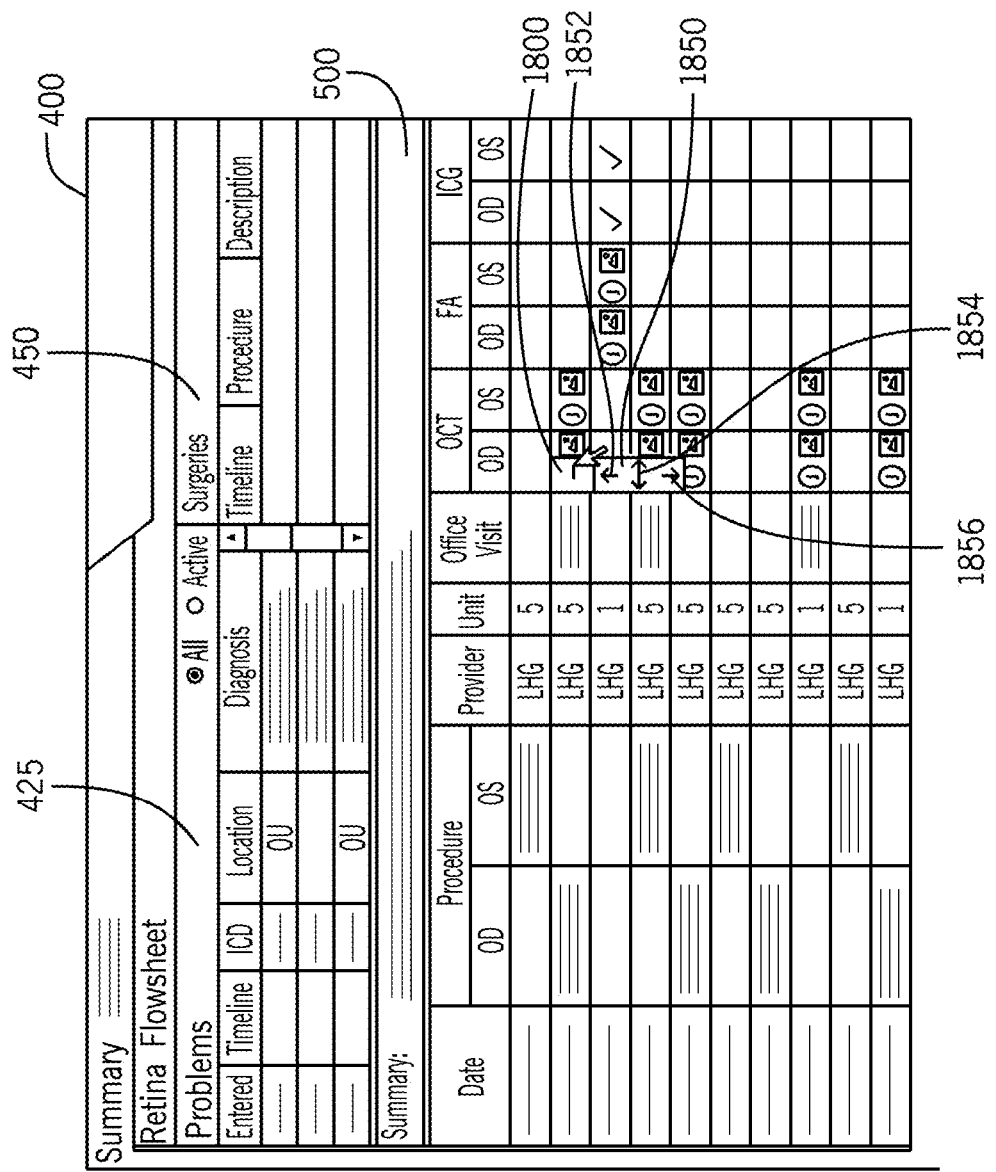
FIG. 9 illustrates a medical record update marker process in accordance with some embodiments of the invention.

In some embodiments, the medical services tracking server system and method can enable a user to update information displayed in the medical tracking display window 500. For example, in some embodiments, a user can update information related to a medical diagnosis and/or information related to a medical test or other service or procedure. For example, FIG. 9 illustrates a medical record update marker process in accordance with some embodiments of the invention. The medical record dashboard 400, including problems window 425, surgeries window 450, and summary window 475 is shown with a record update marker 1800 being accessed by a user and displaying a update marker selection tab 1850. In some embodiments, the update marker selection tab 1850 can include a user-selectable marker or icon. For example, in some embodiments, update marker selection tab 1850 can include a selectable diagnosis indicator 1852, a selectable diagnosis indicator 1854, and/or a selectable diagnosis indicator 1856. In some embodiments, the selectable diagnosis indicators 1852, 1854, 1856 can provide a graphical representation of a medical diagnosis, outcome, or test. For example, in some embodiments, the diagnosis indicators 1852, 1854, 1886 can provide a visual representation of an improvement of a medical problem, disease, or symptom, or a worsening of a medical problem, disease, or symptom. Further, in some embodiments, the diagnosis indicators 1852, 1854, 1856 can provide a visual representation of a medical problem, disease, or symptom that is stable or substantially unchanged. In some embodiments, the diagnosis indicators 1852, 1854, 1856 can provide a visual representation directly related to one or more variables of a physical test. For example, in the field of ophthalmology, some imaging tests can provide an analysis of the thickness of the retina related to an eye disease such as macular degeneration. In some embodiments, an increase in thickness can represent a worsening of the condition, whereas a decrease in thickness can represent an improvement. A stable or unchanged thickness can indicate the disease is responding to treatment or is in remission. Further, by using data visualization techniques such as by using a color change or other method (e.g., such as using italics, bold text, and/or underlined text), a particular important change in a test can be marked for internal reference alerting a physician to the tests or procedures that are important and to take note for future reference. Further, in some embodiments, the diagnosis indicators 1852, 1854, 1856 can comprise a color and/or graphical change providing a visual representation of items billed, items not billed, or tests needing reports or interpretations are required. A color change or data visualization method (e.g., such as using italics, bold text, and/or underlined text) can also tell a physician if a test or procedure was billed, rejected, or if an interpretation needs to be made.

As an example embodiment, the diagnosis indicators 1852, 1854, 1856 can provide a visual representation of the status of a patient with an eye disease such as macular degeneration. For example, in some embodiments, the diagnosis indicators 1852, 1854, 1856 can be selected from the update marker selection tab 1850 when the user intends to indicate a worsening of the condition (e.g., where the thickness of the retina is increasing). In some embodiments, any of the diagnosis indicators 1852, 1854, 1856 can be color-coded to represent a status or provide a visual indicator of a medical condition, test, or diagnosis linked to the diagnosis indicators 1850. For example, in some embodiments, the diagnosis indicator 1852 can be color coded red and the diagnosis indicator 1856 can be color-coded green. Further, the diagnosis indicator 1854 can be color-coded blue or black. In some other embodiments, the diagnosis indicator 1852 can be color coded green and the diagnosis indicator 1856 can be color-coded red. In other embodiments, other graphical markers or icons can be used, and/or other colors can be used to differentiate the diagnosis indicators 1852, 1854, 1856. Further, in some embodiments, in addition to or in place of using a color differentiation between the diagnosis indicators 1852, 1854, 1856, one or more of the diagnosis indicators 1852, 1854, 1856 can flash or pulsate.

Figure 10A:
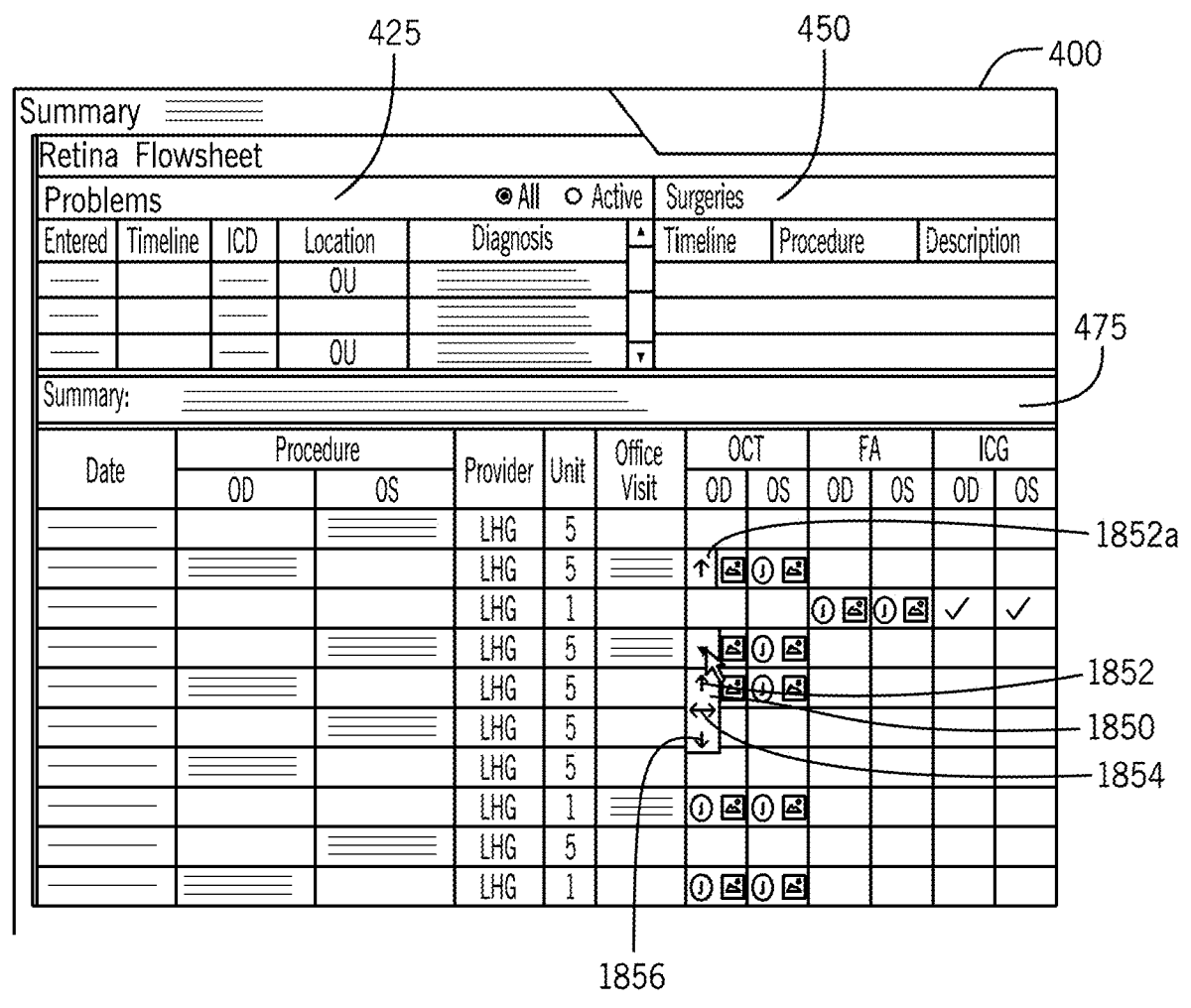

In some embodiments, the medical services tracking server system and method can enable a user to provide a plurality of updates to information displayed in the medical tracking display window 500. For example, in some embodiments, a user can update information related to a medical diagnosis and/or information related to a medical test or other service or procedure, and subsequently provide further updates to the same information or to other information. For example, FIG. 10A illustrates a medical record update marker process in accordance with some embodiments of the invention including medical record dashboard 400, with problems window 425, surgeries window 450, summary window 475, and medical tracking display window 500. The medical tracking display window 500 depicts diagnosis indicator 1852a representing previously updated information. The medical tracking display window 500 also illustrates a user updating information with a process described above using the update marker selection tab 1850 comprising a selection of diagnosis indicator 1852, diagnosis indicator 1854, or diagnosis indicator 1856.

Figure 10B:
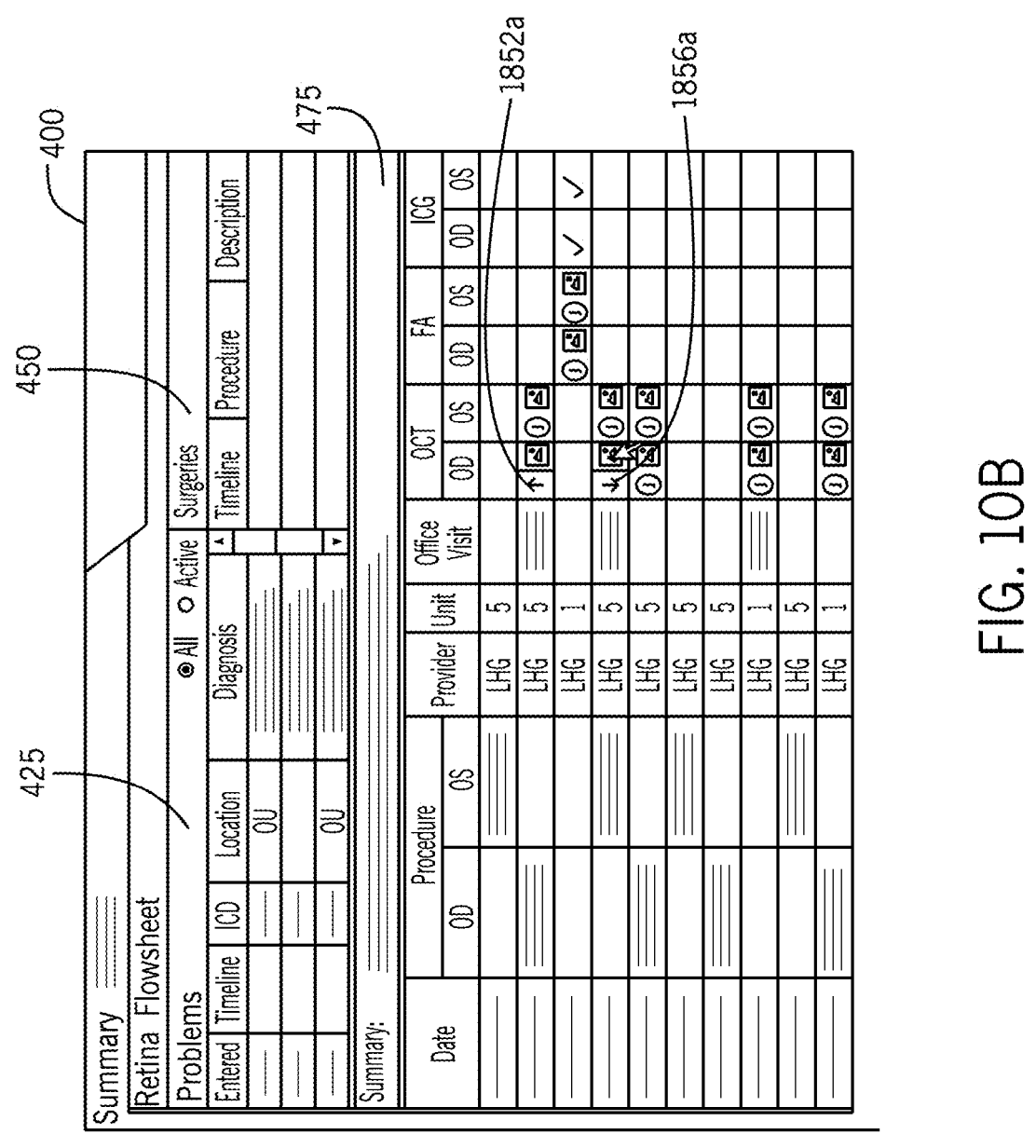

Further, FIG. 10B illustrates a medical record update marker process in accordance with some embodiments of the invention. Following the medical record update marker process shown in FIG. 10A, in some embodiments, the medical record dashboard 400 including medical record dashboard 400, with problems window 425, surgeries window 450, summary window 475, and medical tracking display window 500 can display diagnosis indicator 1852a and diagnosis indicator 1856a indicative of updated information or status of a patient and/or a patient's disease, test, or medical condition. Further, any ICD code can be inserted.

Figure 11:
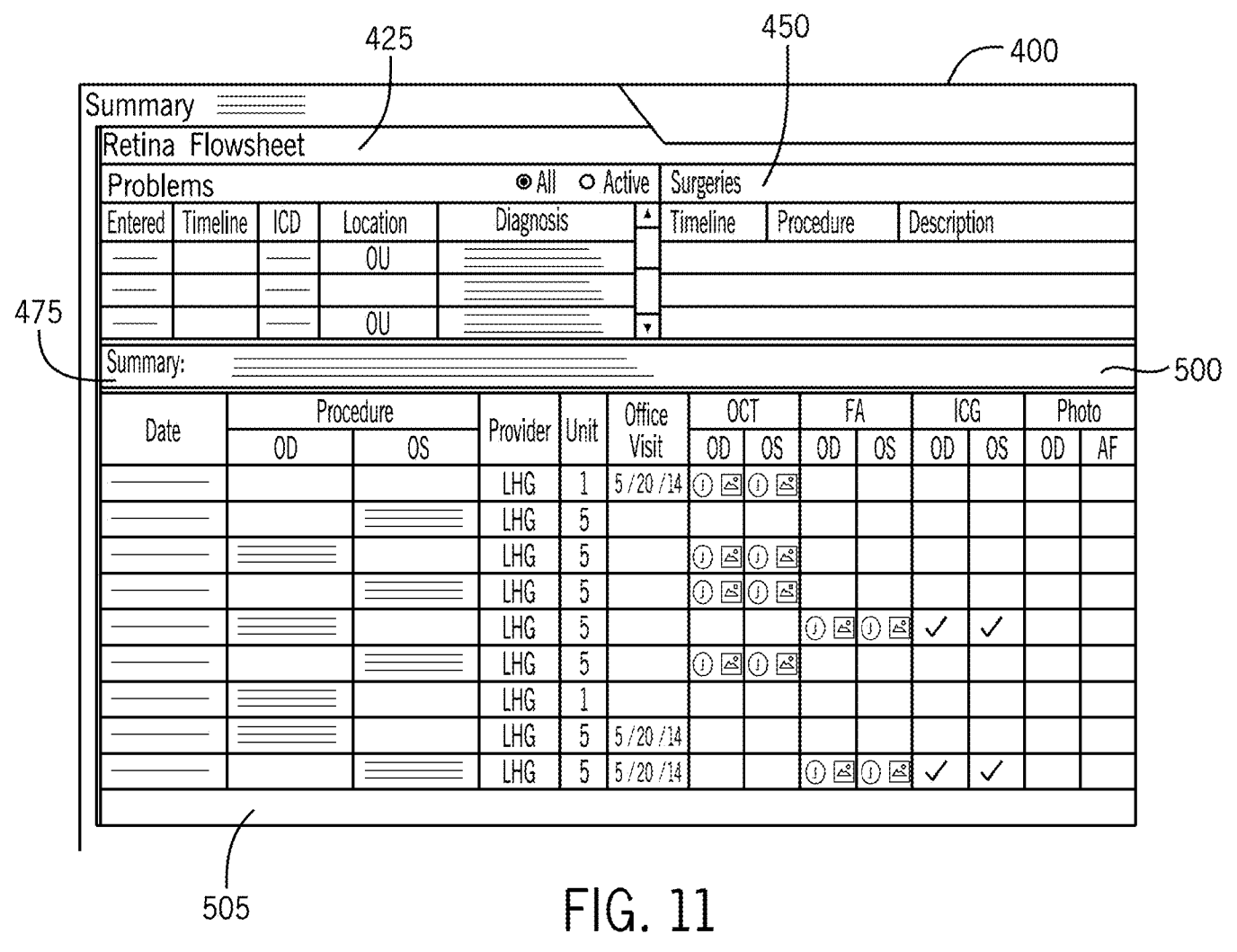

FIG. 11 illustrates a portion of the medical record dashboard 400 of FIG. 4A including a scrolled display in accordance with some embodiments of the invention. In some embodiments, the medical record dashboard 400 including problems window 425, surgeries window 450, summary window 475 can include a medical tracking display window 500 that comprises a scroll display 505. In some embodiments, any information displayed in the medical tracking display window 500 can be scrolled by the user to bring non-visible portions of the medical tracking display window 500 into view. This procedure can enable the user to view the entire history of the patient independent of the number of years of history that is on record.

Figure 12A:
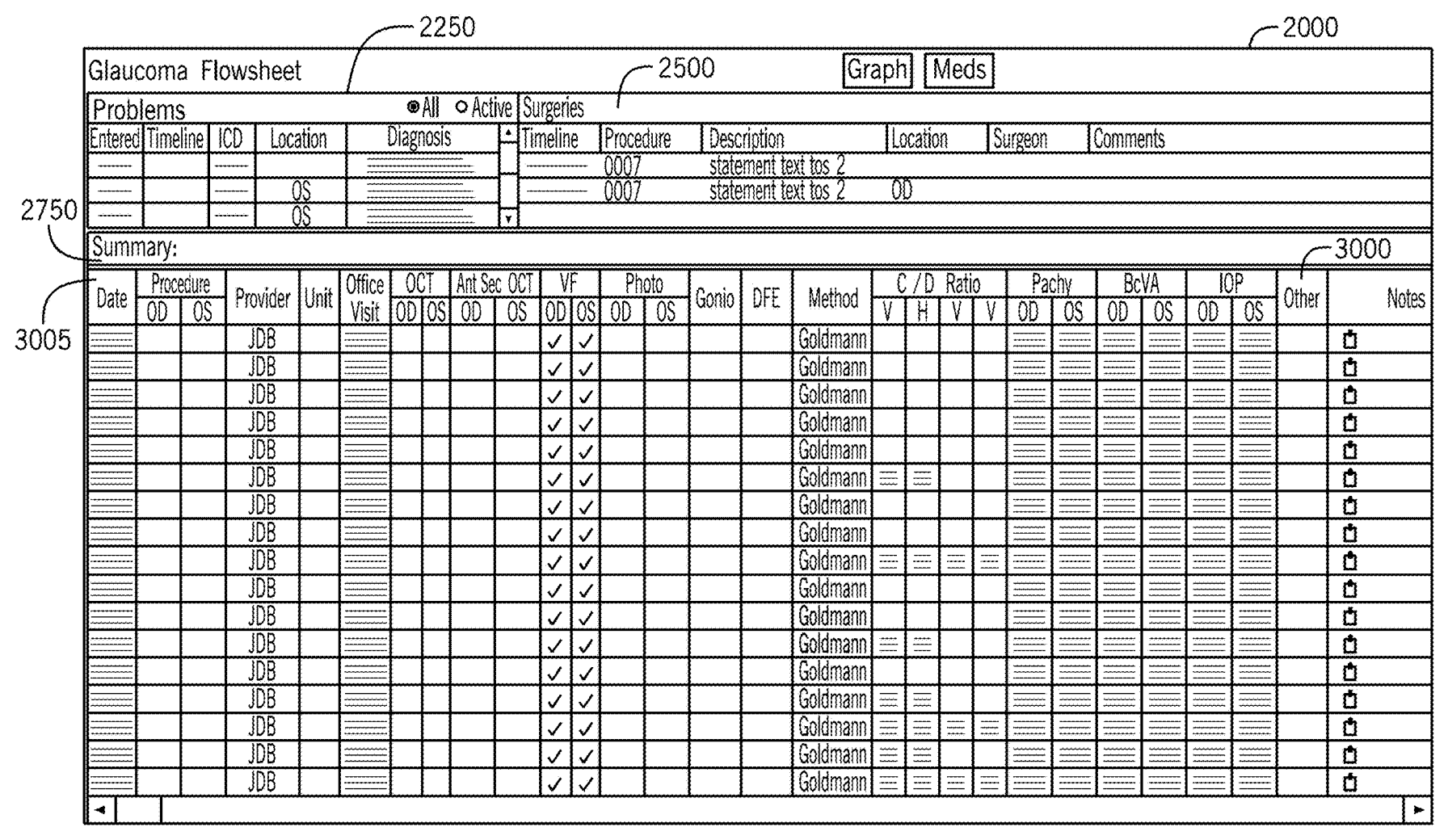

FIG. 12A illustrates a portion of the medical record dashboard 2000 in accordance with another embodiment of the invention. In some embodiments, the medical record dashboard 2000 can display data from one or more medical records, and/or track medical procedures and services based on claims made or billing signed off by a physician for one or more delivered medical procedures or services. Further, in some embodiments of the invention, the medical record dashboard 2000 can be auto-populated as a function of claims made or billing signed off by a physician, auto-populated from any portion of a selected chart. In this instance, any data displayed within the medical record dashboard 2000 can be derived from one or more claim records that have been billed for one or more procedures or services have previously been provided to the patient. In reference to the medical record dashboard 2000 and/or the previously described medical record dashboard 400, in some embodiments of the invention, auto-populating visits by actual claims made or billings signed off by a physician, by definition occurs after the visit with the patient. In some embodiments, the medical services tracking server system and method can auto-populate the some information at the time the patient is seen, or shortly thereafter, or even before in preparation for a visit (i.e., lab results), so that even if a patient is not seen on a particular day, the user (e.g., medical provider) can view the displayed information in the table for information. For example, in some embodiments, information related to vision can be made with the current date at the time patient is seen. In some embodiments, a user or user's assistant can update the medical services tracking server system and method with medical tests or test results (e.g., a vision test) as they are performed or shortly thereafter (i.e., on the same day). In this example, this information can immediately trigger the current date and auto-populate the vision column. This information can then be immediately viewed by a user and/or medical provider, and can be updated with notes or comments or other information as the user and/or medical provider is attending to the patient. Further, after the claim has been made for any diagnostic tests or examinations or procedures that have not yet been billed, the date will then auto-populate in the future with the other related columns. In some embodiments, while examining a patient, important information and/or certain parameters that are critical to follow can be immediately updated to the medical services tracking server system and method. Using these procedures, the medical services tracking server system and method can enable the medical provider to review the patient's medical history, treatment history, and instantly see items of importance on the day they're examining a patient. For example, the user and/or medical provider can be enabled by the medical services tracking server system and method, on the day the patient is examined, to review information such as a vision or glaucoma table, intraocular pressure, blood pressure, blood sugar, etc. When billing claims are made, further information is filled to complete the billed claims record. As a further example, a patient may be seen a few days apart and the diagnostic tests etc. and claims have not yet been made, however the medical services tracking server system and method can be configured to show that the patient was seen that day (e.g., with a vision, pressure test, etc.), and the medical services tracking server system and method can enable a user (such as a physician) to interpret and/or add special notes on the day they see a patient or before they see the patient rather than waiting to make some notes when a claim is actually generated.

In some embodiments, is a medical office wishes to communicate results or a test (e.g., a pathology result or test) a blinking cursor can appear to alert a lab physician to confirm done or other correspondence can be auto-populated into other portions of the EMR the EMR. Also any written or type correspondence or any links to dictated information using voice recognition coupled to or integrated with the medical services tracking server system and method. The display can include information including components where there is a summary of the patient's problem list that a user can input patient information and constantly update and change. Further, this information can be auto-populated with the touch of a button into a designated location such as the current plan documenting the patient's current visit (thus aiding documentation for the current visit). Further, whatever is important for a user to input into the day's visits for documentation can be initially inputted in the table, and then permanently into the day's patient visits. Further, the summary section of the medical record dashboard 4400 can be constantly fluid, and can be changed at every visit rather than being written to an unchangeable document or file (e.g., such as a PDF). Any patient data that is inputted, received, analyzed, or created can be auto-populated into any portion of the dashboard 4400. The medical services tracking server system and method can auto-populate in a one-way or two-way direction in various data fields related to information in any patient information via an electronic dataflow established between the medical services tracking server system and method and one or more computer systems of servers that comprise patient information (e.g., such as electronic medical records). The dataflow can comprise a two-way flow from the source of patient data to the medical services tracking server system and method, and from the medical services tracking server system and method to the source including another electronic system or server, or another user, observer, or other 3rd party.

By following a patient on the day of delivery (e.g., for a vision intraocular pressure or anything else) can enable the user and/or medical provider to see the diagnostic test on same day even though it has not been billed. Further, this procedure can enable the medical provider to optionally add a note (as described earlier) and allow free hand typing at the end of the line.

In some embodiments, medical information populated within the medical services tracking server system and method (e.g., shown as visual cues, icons, or markers 885 representing medical services, procedures or tests performed or provided to the patient) can include a visual marker such as a red dot. In some embodiments, the medical services tracking server system and method can display the red dot until a claim is actually made at which time the medical services tracking server system and method can display can display a green dot (i.e., the medical services tracking server system and method can convert the red dot to a green dot). In some embodiments, by clicking on the dot, the user can toggle between the payment screen and the medical tracking display window 500, 3000. This can allow medical providers to improve patient care, to review the actual picture of a diagnostic test that is displayed within the medical tracking display window 500, 3000, to review other diagnostic tests results, and to compare to what happened on other days. In some embodiments, at any time, a medical provider can click on the dot to access a display where the claim is billed, and any payment that was made can be displayed. This process can help to reduce medical errors enabling medical providers to quickly review the billings and claims made or billings signed off by a physician and payment portions of the medical services tracking server system and method. Further, this procedure serves as an additional tool to minimize coding, compliance, and medical treatment errors, as the medical services tracking server system can provide a quick reference tool that can pull all critical medical and compliance data from the patients EMR chart into a concise and clear table.

In some embodiments, the medical record dashboard 2000 can display information related to medical procedures or services in relation to care of a patient with glaucoma. In some embodiments, the medical record dashboard 2000 can display various windows and sub-windows based on a user preference and/or current or previous user interaction with the medical record dashboard 2000. Some embodiments include a medical record dashboard 2000 that comprises information columns 2050 including a problems window 2250 and/or a surgeries window 2500 where information related to a patient's medical problems and surgeries can be displayed. In some embodiments, the medical record dashboard 2000 can include a summary window 2750 enabling a user to view and edit summary information related to the patient, any details of care provided to the patient, and/or and any medical diagnosis information prepared by a medical practitioner. Further, the medical record dashboard 2000 can also display detailed information related to any medical procedures or services provided to the patient, including procedures or services that are auto-populated by claims made or billing signed off by a physician as detailed above or other method. For example, in some embodiments, the medical record dashboard 2000 can display a medical tracking display window 3000 including a plurality of information columns 3005. In some embodiments, the medical tracking display window 3000 can be scrolled by the user to display other portions of the medical tracking display window 500.

In some embodiments, the medical record dashboards 400, 2000 can also display detailed information related to notification of payment of any medical procedures or services provided to the patient, including procedures or services that are auto-populated by claims made or billing signed off by a physician as detailed above or other method. Moreover, the medical record dashboards 400, 2000 can enable a user to access and/or track the status of the billing and payment process at any point in time. For example, in some embodiments, the medical record dashboards 400, 2000 can access and view any patient encounter form (i.e. a superbill), any claims made to a clearing house, any updates on accepted or rejected bills from the clearing house, any claims made to an insurance company, and/or any payments received for any claims made.

Figure 12B:
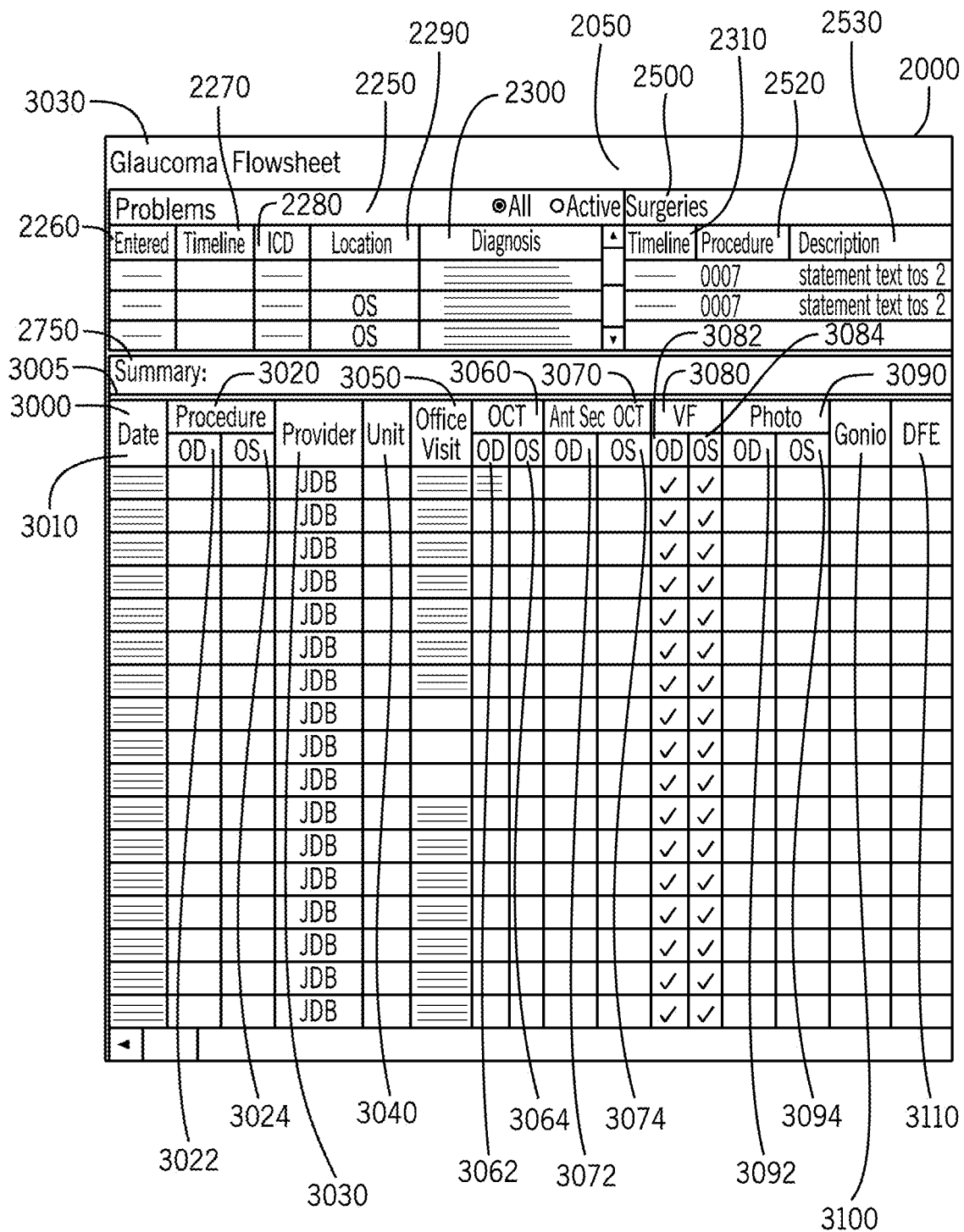
FIG. 12B illustrates a portion of the medical record dashboard of FIG. 12A in accordance with some embodiments of the invention.

FIG. 12B illustrates a portion of the medical record dashboard 2000 of FIG. 12A in accordance with some embodiments of the invention. As shown, the problems window 2250 can include a date and time information in entered date column 2260, a timeline column 2270, an "ICD" column 2280 for ICD code information, location of the problem or disorder (shown as "OD", "OS", "OU"

identifying right eye, left eye, both eyes) (column 2290), and a diagnosis column 2300 for detailing information related to an initial diagnosis or final diagnosis of a patients problem or disorder. Further, the surgeries window 450 can include information related to services or procedures were provided to the patient (procedure columns 2520), a description of the services or procedures performed (description columns 2530), and when the services or procedures were provided to the patient (shown as timeline columns 2310), and can include a surgical report that can be brought up and viewed by the user.

Referring to the medical tracking display window 3000 of dashboard 2000, the information columns 3005 can include a date column 3010, and a procedure column 3020 illustrating or providing access to information detailing one or more procedures performed on the patient. Further, the procedure column 3020 can include an "OD" column 3022, and "OS" column 3024 providing right and left eye procedure information. In some embodiments, information related to the medical provider, location where the procedure was performed, and office visit information can be provided to the user in the provider column 3030, and unit column 3040, and office visit column 3050.

In some embodiments of the invention, the medical tracking display window 3000 can enable a user to view information related to tests and procedures performed on the patient including, but not limited to one or more medical imaging procedures such as an optical coherence tomography ("OCT"), or fluorescein angiography ("FA"), and/or indocyanine green chorioangiography ("ICG"). In some embodiments, medical procedures performed (including any of the aforementioned medical imaging procedures) that have been billed and claimed can be viewed or accessed by a user within any of the "OCT" column 3060 (shown split as an "OD" column 3062 and "OS" column 3064), an "Ant Seg OCT" column 3070 (split as an "OD" column 3072 and "OS" column 3074).

In some embodiments, if visual function tests were performed, information can be viewed or accessed in the "VF" column 3080 (including an "OD" column 3082, and/or an "OS" column 3084. Some embodiments include a photo column 3090 configured to enable a user to access any photographic images of the patients eyes including optical and/or auto-fluorescent images of the eyes ("OD" column 3092 and "OS" column 3094). Further, some embodiments include a Gonio column 3100 providing access to gonioscopy data and/or information related to a dilated fundus examination ("DFE" column 3110). In some embodiments, the surgeries window 2500, can include location column 2540, surgeon column 2550, and a comments column 2560 (shown in FIG. 12C).

Figure 12C:
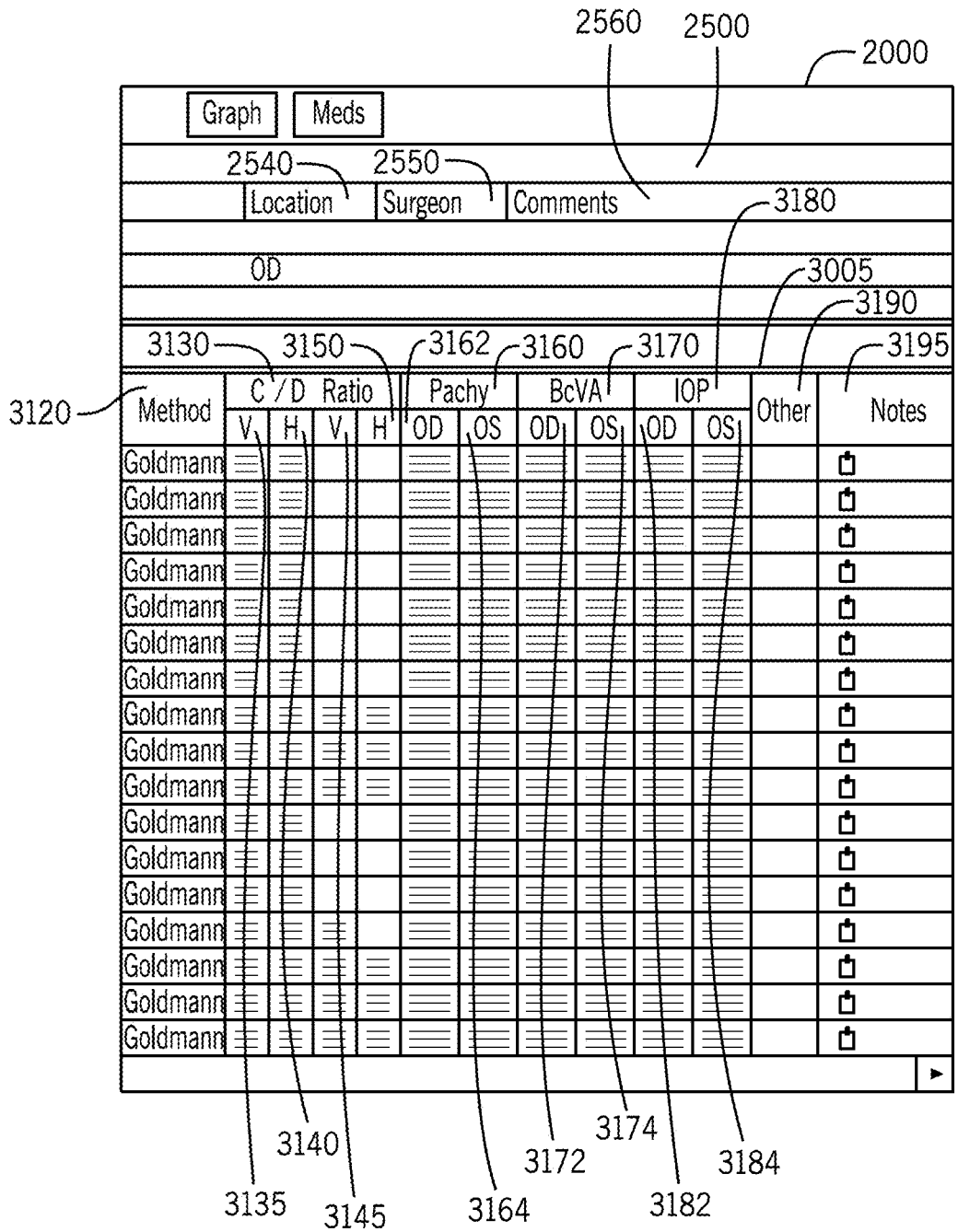
FIG. 12C illustrates a portion of the medical record dashboard of FIG. 12A in accordance with some embodiments of the invention.

In some embodiments of the invention, the medical tracking display window 3000 can enable a user to view information related to tests and procedures performed on the patient including a cup-to-disc ratio ("C/D") to assess the progression of glaucoma, Pachymetry data ("Pachy"), refraction test information such as best-corrected visual acuity ("BCVA"), and/or intraocular pressure (TOP) data. For example, FIG. 12C illustrates a portion of the medical record dashboard of FIG. 12A in accordance with some embodiments of the invention and shows method column 3120, "C/D ratio" column 3130, "Pachy" columns 3160, "BcVA" columns 3170, and "IOP" columns 3180. In some embodiments, the "C/D ratio" column 3130 includes "V" column 3135, "H" column 3140, "V" column 3150, and "H" column 3150. Further, in some embodiments, the "Pachy" columns 3160 includes "OD" column 3162, and "OS" column 3164. In some embodiments, the "BcVA" columns 3170 includes "OD" columns 3172, and "OS" columns 3174. Some embodiments include "IOP" columns 3180 including "OD" columns 3182, and "OS" columns 3184. In some embodiments, other columns 3190 can be used to add additional test information. Further, the medical tracking display window 3000 can also include a notes column 3195 for accessing and updating notes related to tests and medical diagnosis. In some embodiments, the tracking display window 3000 can be updated with comments and notes as described earlier with respect to tracking display window 400.

In some embodiments of the invention, the medical services tracking server system and method can display and auto-populate the medical record dashboard 400 and/or the medical record dashboard 2000 with more than one patient information. For example, in some embodiments, any windows, sections, or columns of the medical record dashboard 400, 2000 can display information related to a plurality of patients. Any patient data that is inputted, received, analyzed, or created can be auto-populated into any portion of the dashboard 400, 2000, where the medical services tracking server system and method can auto-populate in either a one-way or a two-way direction. Thus, data fields related to information in any patient information can be communicated via an electronic dataflow established between the medical services tracking server system and method and one or more computer systems of servers comprising patient information (e.g., such as electronic medical records).

Further, in some embodiments of the invention, any information displayed by the medical services tracking server system and method can display and auto-populate the medical record dashboard 400 and/or the medical record dashboard 2000 as a function of patients seen during a specified time period. In some other embodiments of the invention, the medical services tracking server system and method can display and auto-populate the medical record dashboard 400 and/or the medical record dashboard 2000 as a function of a specified disease and/or diagnosis. For example, in some embodiments, the medical services tracking server system and method can display and auto-populate the medical record dashboard 400 and/or the medical record dashboard 2000 as a function of a CPT code or ICD code from input received from a physician or other medical practitioner or provider. For instance, every patient who has the diagnosis of diabetes with their name and the date last scene is auto-populated. Certain parameters that may need to be followed by the user from all of their patients with this condition can be auto-populated. For example, in the case of patients with diabetes, parameters can include how often they've missed appointments, blood sugar, hemoglobin A-1 C, medications, major new medical complications such as heart attack, stroke, amputations, blindness, each of which can be auto-populated and followed to enable the user to see how all their patients are doing. In some embodiments, the user can also receive a daily report on all the patients they've seen, what the diagnosis codes are and what CPT, ICD, or office visit billing codes were done. In some embodiments, any report or diagnostic test can be sent to a patient portal, to an email server, and/or as a fax. Further, the user can be alerted when the claims go out and when they're actually paid. For example, in some embodiments, the above described methods of display can provide a mechanism for determining payments to the user, and if claims are being made for each patient seen in any particular day, week or month.

Examples of the aforementioned examples of displayed data sorted and viewable by patient, disease time-period, physician, etc., are shown in FIGS. 12D and 12E. For example, FIG. 12D illustrates a portion of a medical record dashboard 3200 for display as a function of disease or patient in accordance with some embodiments of the invention. Further, FIG. 12E illustrates a portion of a medical record dashboard 3600 for display as a function of patients or physician or disease state in accordance with some embodiments of the invention. In some embodiments, the medical record dashboards 3200, 3600 can be displayed overlaid on a previously viewed dashboard such as medical record dashboard 400, 2000. For example, in some embodiments, the medical record dashboards 3200, 3600 can be displayed in the medical tracking display window 500. In other embodiments, the medical record dashboards 3200, 3600 can be displayed independently from the medical record dashboard 400, 2000, and the user can toggle a display of any of the medical record dashboard 400, 2000, 3200, 3600.

Referring to FIG. 12D, including providing a list of patients 3205, within column 3210, an entire day of patients listed by date can be provided or the list can comprise a single patient with multiple visits. For example, in some embodiments, within column 3220, an office visit and any items billed for a routine examination day and any other CPT codes billed that day can be displayed. Some specialties will have many CPT codes during an office visit (e.g. Ophthalmologists, whereas others (e.g., Gastroenterologists) may have four during an office visit. In some embodiments, column 3230 can include the procedures that a physician may perform, and are usually not on the same day as the exam (these are GI physicians examples). In some further embodiments, the column 3240 can include various important parameters that can be followed for a specific patient. Some embodiments include column 3250 that includes where a physician writes notes about patient care issues. In some embodiments of the invention, column 3260 can takes the user to that patient's personal EMR or review table and can also send a message to the patient. In some embodiments, the column 3270 can takes the physician to the charge payment history of the patient, and also a message can be sent to the billing department from this table. In some embodiments, columns 3220, 3230 can be colored 'black' when a claim is made, and can be colored 'green' if paid, and can be colored 'yellow' if a payment is pending, and can be colored 'red' if payment denied by one rendition, e.g., physician reconciliation report of messages sent individuals for follow up, and/or a report of all the message activity from any given day.

Referring to FIG. 12E, including example embodiments related to patients with diabetes, the display for patients 3610 can include can include a variety of medical, billing, and insurance related information. This medical record dashboard 3600 can be display as shown, or can be sorted based on any of the data columns. For example, the patients 3610 can be shown including information displaying insurance coverage 3620, date of diagnosis of diabetes 3630, the patient's age 3640, the patient's weight 3650, the patient's height 3660, their body mass index 3670, their initial presenting HbgA1C 3680, their most recent HbgA1C 3690, their hypertension status 3692, their recent blood pressure 3694, their All ICD diagnosis 3696 and their current or past medications 3698. In some embodiments, the medical record dashboard 3600 can be reconfigured to shown patients 3610 sorted by any of the columns 3620, 3630, 3640, 3650, 3660, 3670, 3680, 3690, 3692, 3694, 3696, 3698.

In some embodiments of the invention, the medical services tracking server system and method can enable a user to update a medical record dashboard 400 and/or the medical record dashboard 2000 to be mark personalized to the next treating physician or patient to follow progression changed outcomes. This will be used to access quality of care and prove effectiveness and results resolution, and can be used for negotiating with insurance carriers or for performance research. For example, anything can be tracked or personalized to the needs of the treating physician or patient to follow progression, changes, and outcomes. This can be used to assess quality of care and prove effectiveness and results of treatment. Quality outcome measures are critical for all practices to start to follow as this improves patient care, and in the future, a physician's financial compensation from insurance companies, or any penalization will be determined based on the quality of care metric. Further, physicians who participate in clinical research must follow defined parameters over time as they learn whether a particular drug, or device, or other item being investigated actually improve changes or worsens particular parameters. As described earlier, in some embodiments, the information that is auto-populated can include patient outcome summaries. In some embodiments, the medical service tracking server system and method canprocess patient outcomes and display an analysis of patient outcomes based on patient information from treatment summaries, and/or diagnosis summaries, and/or patient feedback summaries, and/or other physician summaries or treatments. The patient outcomes can include or comprise physician quality reporting system (PQRS) quality measures, and calculated or reported patient outcomes can include or comprise PQRS measures codes.

By way of example in FIG. 4C, 1100 vision is followed, and other column 1200, many different parameters that may change over time can be added. For example, as described earlier with respect to participation in clinical research studies, other factors followed such as central macular thickness ("CMT"), or ischemic index ("ISI") (% and A scan in millimeters) can be followed. Therefore, every time the patient comes in to be examined, the table can serve the multi-purpose of treating the patient, and for inputting research data from the office visit right into the table. This can then auto-populate into another portion of the EMR or derive these numerical values and place them into the research Excel spreadsheet. Also it could go the other way, where if the Excel research spreadsheet can be also have the data inputted into the review table.

In some embodiments of the invention, the medical services tracking server system and method can enable a date alert or self-destruction of any information or data entered or auto-populated in the medical record dashboard 400 and/or the medical record dashboard 2000. For example, in some embodiments, any message, or note, or summary, or any medical data can include a date alert and/or a self-destruct function that can instruct the medical services tracking server system and method to remove and/or delete information from the medical record dashboard 400 and/or the medical record dashboard 2000. In other embodiments, the historical date and/or an alert or warning can be provided with any auto-populated or user-summoned information to assist the user with an assignment of relevancy to any data being reviewed prior to, during, or after a patient visit or examination. In some embodiments, this feature can optimize the standard of care being delivered by the user. For instance, this feature can help monitor preferred practice patterns or serve as a reminder on information needed for clinical review.

Figure 13A:
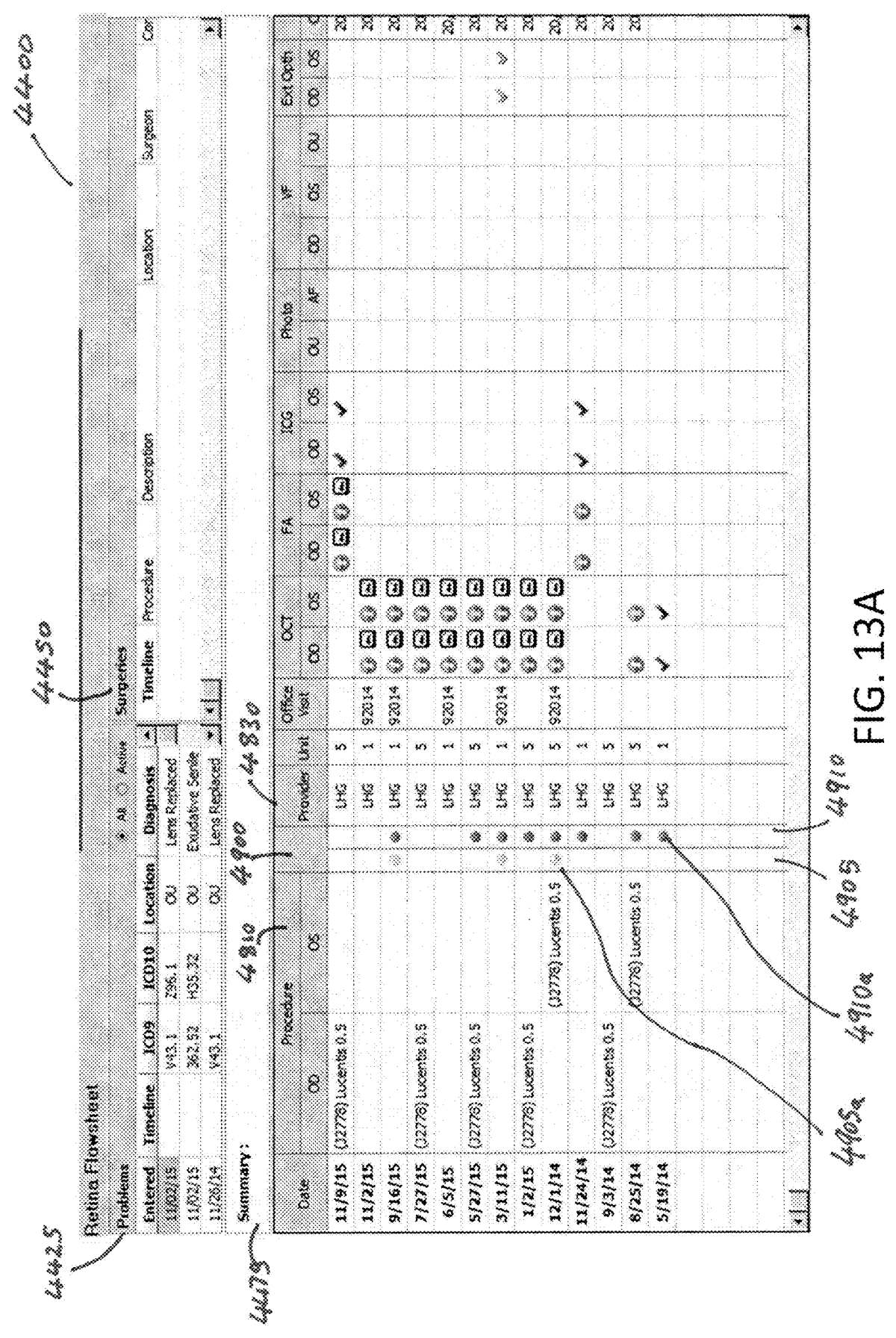

In some embodiments of the inventor, the medical services tracking server system and method can enable a user to access a detailed ledger comprising financial information related to one or more procedures. In some embodiments, the ledger can be accessed from a medical record dashboard. Further, in some embodiments, the dashboard can include at least one visual indication of a payment for services provided, where detailed information of the charges, payments, write-offs, adjustments, and balances can be accessed and displayed. For example, FIG. 13A illustrates a medical record dashboard 4400 in accordance with some embodiments of the invention. In some embodiments of the invention, the medical record dashboard 400 illustrated in FIG. 4A can comprise, include, or be replaced by the medical record dashboard 4400. In some embodiments, the medical record dashboard 4400 can be access as described for the medical record dashboard selection window of FIG. 3. In some embodiments, the medical record dashboard 400 can be displayed by the user following the user's selection of at least one medical record dashboard from the medical record dashboard selection window 300. For example, in some embodiments, the user can select "Retina Flowsheet" 305 to access and/or launch the medical record dashboard 4400

In some embodiments, the medical services tracking server system and method display a medical record dashboard 4400 including a display of data from one or more medical records, and/or track medical procedures and services based on claims made or billing signed off by a physician for one or more delivered medical procedures or services. Some embodiments of the invention include a medical service tracking server system and method that can dynamically link to various external databases comprising patient information that can be displayed in the medical record dashboard 4400. For example, in some embodiments, the medical service tracking server system and method can function as a portal to patient information prepared by the user or patient information from other sources. Further, in some embodiments of the invention, the medical record dashboard 4400 can be auto-populated as a function of claims made or billing signed off by a physician. In this instance, any data displayed within the medical record dashboard 4400 is derived from one or more claim records that have been billed for one or more procedures or services have previously been provided to the patient. In some other embodiments, auto-population can be enabled in both directions interacting as a switchboard between the entire EMR and the medical record dashboard 4400 along with what is added to any window, sub-window, column or entry in the medical record dashboard 4400 being automatically added to the appropriate part of the chart for documentation. In some embodiments, the medical record dashboard 4400 can display information related to medical procedures or services in relation to retinal eye care of a patient. In other embodiments, the medical record dashboard 400 can display information related to medical procedures or services in relation to any kind of medical care of a patient.

In some embodiments, the medical record dashboard 4400 can display various windows and sub-windows based on a user preference and/or current or previous user interaction with the medical record dashboard 4400. For example, in some embodiments, the medical record dashboard 4400 can display a problems window 4425 and/or a surgeries window 4450 where information related to a patient's medical problems and surgeries can be displayed.

In some embodiments, the medical record dashboard 4400 can display information including components where there is a summary of the patient's problem list that a user can input patient information and constantly update and change. Further, this information can be auto-populated with the touch of a button into a designated location such as the current plan documenting the patient's current visit (thus aiding documentation for the current visit). Further, whatever is important for a user to input into the day's visits for documentation can be initially inputted in the table, and then permanently into the day's patient visits. Further, the summary section of the medical record dashboard 4400 can be constantly fluid, and can be changed at every visit rather than being written to an unchangeable document or file (e.g., such as a PDF). For example, in some further embodiments, the medical record dashboard 4400 can include a summary window 4475 enabling a user to view and edit summary information related to the patient, any details of care provided to the patient, and/or and any medical diagnosis information prepared by a medical practitioner. Further, the medical record dashboard 4400 can also display detailed information related to any medical procedures or services provided to the patient, including procedures or services that are auto-populated by claims made, or billings or payments including billing signed off by a physician as detailed above. All of the features of the medical record dashboard 400 as described earlier can be provided in the medical record dashboard 4400

Some additional features include the dashboard 4400 displaying at least one visual indication of a payment for services provided on the dashboard 4400. Further, the user can be provided with access to a detailed ledger comprising financial information related to one or more procedures. For example, in some embodiments, the dashboard can comprise a payment indicator column 4900 including one or more indicator and/or access icons. For example, in some embodiments, the payment indicator column 4900 can comprise a column 4905a that can be populated with one or more indicator icons. In other embodiments, the column 4905b can be provided with one or more indicator or access icons. In some embodiments, the one or more indicator or access icons can comprise icons of color such as yellow or green.

The payment indicator column 4900 can be positioned anywhere on the dashboard 4400. In the example embodiments of FIG. 13A, the payment indicator column 4900 can be positioned between the procedure column 4810 illustrating or providing access to information detailing one or more procedures performed on the patient, and information related to the medical provider, provider column 830, that can display the location where the procedure was performed, and office visit information.

In some embodiments, one or more of the icons of the payment indicator column 4900 can be accessed by the user to initiate the medical services tracking server system and method displaying more detailed financial information. An example embodiments is illustrated in FIG. 13B illustrating a ledger window 5000 accessible from the medical record dashboard 4400 of FIG. 13A. In some embodiments, the medical services tracking server system and method can display the ledger window 5000 overlaid onto the medical record dashboard 4400. In other embodiments, the ledger window 5000 can be displayed in place of the medical record dashboard 4400. In other embodiments, the ledger window 5000 can be displayed with the medical record dashboard 4400.

In some embodiments, the ledger window 5000 can include information processed by the medical services tracking server system and method including information related to the date of procedure, description of the procedure, dates entered, a charge type, etc. For example, in some embodiments, ledger window 5000 can include the service to column 5010, entered column 5020, line column 5030, type column 5040, and description column 5050. Further, in some embodiments, the ledger window 5000 can include information related to payments and billing. For example, in some embodiments, the ledger window 5000 can include a display of a charge column 5060, payment column 5070, write-off column 5080, adjustment column 5090, and a balance column 5100. In some embodiments, the user can close the ledger window 5000 and return to the medical record dashboard 4400 at any time. In other embodiments, more than one ledger window 5000 can be displayed based on selections made by the user in the medical record dashboard 4400.

Figure 14:
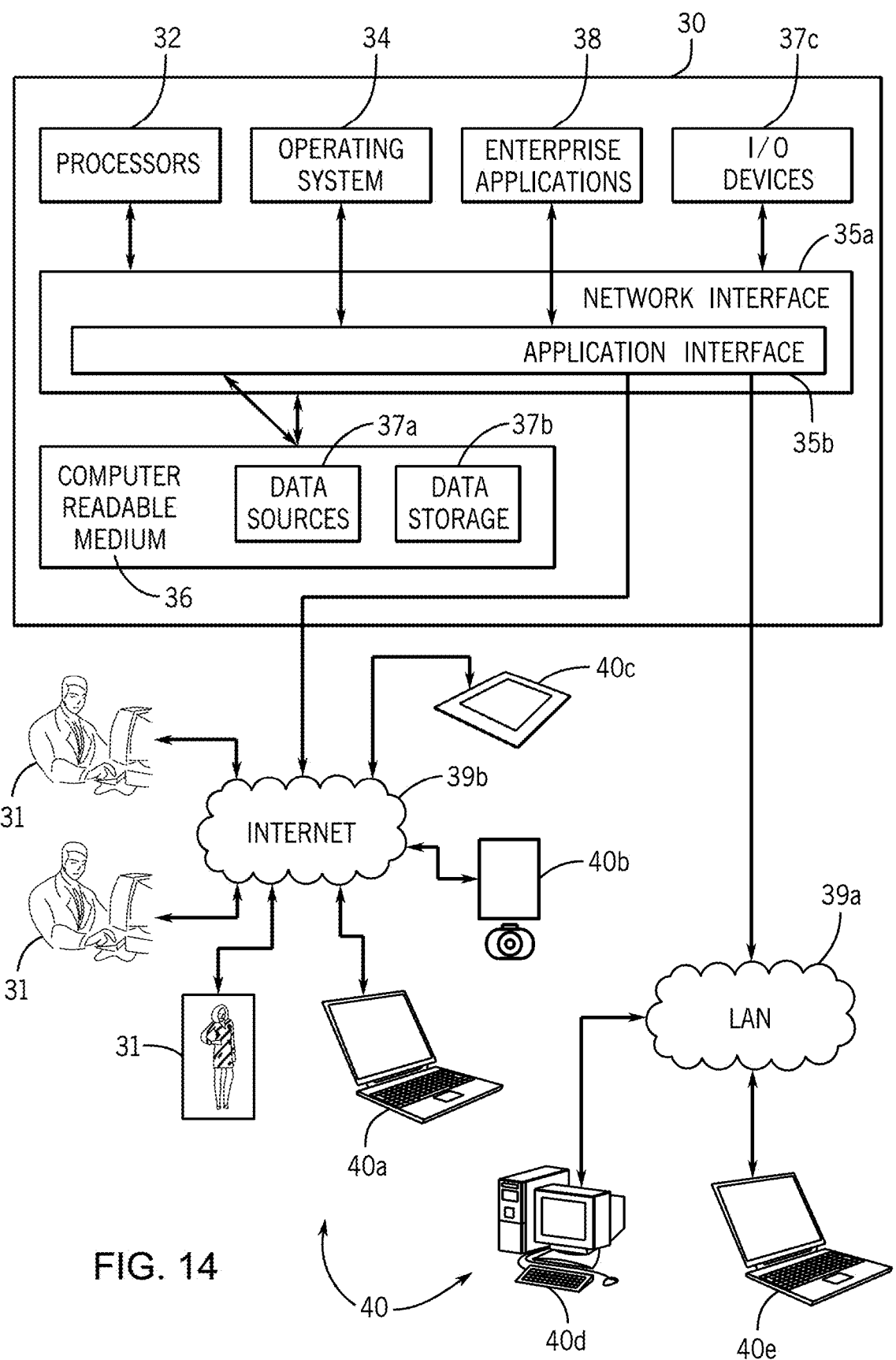
FIG. 14 illustrates a computer server system configured for operating and processing components of the medical services tracking server system and method in accordance with some embodiments of the invention.

FIG. 14 illustrates a computer system 30 configured for operating and processing components of the medical services tracking server system and method in accordance with some embodiments of the invention. In some embodiments, the computer system 30 can process one or more software modules of the aforementioned medical services tracking server system and method and display information related to medical services within at least one graphical user interface. Further, in some embodiments, using the computer system 30, the medical services tracking server system and method can manage the organization of data and data flow between the various components of the medical services tracking server system and method. For example, in some embodiments, the computer system 30 can be configured to process and display the medical record dashboard 400 and/or the medical record dashboard 2000. Further, in some embodiments, the computer system 30 can be configured to process and display auto-populated data within any portion of the medical record dashboards 400, 2000, including, but not limited to the medical tracking display window 500 and/or the medical tracking display window 3000.

In some embodiments, the system 30 can include at least one computing device, including one or more processors 32. Some processors 32 can include processors 32 residing in one or more conventional server platforms. The system 30 can include a network interface 35a and an application interface 35b coupled to at least one processors 32 capable of running at least one operating system 34. Further, the system 30 can include a network interface 35a and an application interface 35b coupled to at least one processors 32 capable of running one or more of the software modules (e.g., enterprise applications 38). Some embodiments of the invention also relate to a device or an apparatus for performing these operations. The apparatus can be specially constructed for the required purpose, such as a special purpose computer. When defined as a special purpose computer, the computer can also perform other processing, program execution or routines that are not part of the special purpose, while still being capable of operating for the special purpose. Alternatively, the operations can be processed by a general purpose computer selectively activated or configured by one or more computer programs stored in the computer memory, cache, or obtained over a network. When data are obtained over a network the data can be processed by other computers on the network, e.g. a cloud of computing resources.

With the above embodiments in mind, it should be understood that the invention can employ various computer-implemented operations involving medical services tracking data stored in computer systems. Moreover, the above-described databases and models throughout the medical services tracking can store analytical models and other data on computer-readable storage media within the system 30 and on computer-readable storage media coupled to the system 30. In addition, the above-described applications of the medical services tracking server system can be stored on computer-readable storage media within the system 30 and on computer-readable storage media coupled to the system 30. These operations are those requiring physical manipulation of physical quantities. Usually, though not necessarily, these quantities take the form of electrical, electromagnetic, or magnetic signals, optical or magneto-optical form capable of being stored, transferred, combined, compared and otherwise manipulated.

Some embodiments include the system 30 comprising at least one computer readable medium 36 coupled to at least one data storage device 37b, and/or at least one data source 37a, and/or at least one input/output device 37c. In some embodiments, the invention embodied by the medical services tracking server system can also be embodied as computer readable code on a computer readable medium 36. The computer readable medium 36 can be any data storage device that can store data, which can thereafter be read by a computer system (such as the system 30). Examples of the computer readable medium 36 can include hard drives, network attached storage (NAS), read-only memory, random-access memory, FLASH based memory, CD-ROMs, CD-Rs, CD-RWs, DVDs, magnetic tapes, other optical and non-optical data storage devices, or any other physical or material medium which can be used to tangibly store the desired information or data or instructions and which can be accessed by a computer or processor (including processors 32).

In some embodiments of the invention, the computer readable medium 36 can also be distributed over a conventional computer network via the network interface 35a so that the medical services tracking server system embodied by the computer readable code can be stored and executed in a distributed fashion. For example, in some embodiments, one or more components of the system 30 can be tethered to send and/or receive data through a local area network ("LAN") 39a. In some further embodiments, one or more components of the system 30 can be tethered to send or receive data through an internet 39b (e.g., a wireless internet). In some embodiments, at least one software application 38 running on one or more processors 32 can be configured to be coupled for communication over a network 39a, 39b. In some embodiments, one or more components of the network 39a, 39b can include one or more resources for data storage, including any other form of computer readable media beyond the media 36 for storing information and including any form of computer readable media for communicating information from one electronic device to another electronic device.

In some embodiments, the network 39a, 39b can include wide area networks ("WAN"), direct connections (e.g., through a universal serial bus port) or other forms of computer-readable media 36, or any combination thereof. Further, in some embodiments, one or more components of the network 39a, 39b can include a number of client devices which can be personal computers 40 including for example desktop computers 40d, laptop computers 40a, 40e, digital assistants and/or personal digital assistants (shown as 40c), cellular phones or mobile phones or smart phones (shown as 40b), pagers, digital tablets, internet appliances, and other processor-based devices. In general, a client device can be any type of external or internal devices such as a mouse, a CD-ROM, DVD, a keyboard, a display, or other input or output devices 37c. In some embodiments, various other forms of computer-readable media 36 can transmit or carry instructions to a computer 40, including a router, private or public network, or other transmission device or channel, both wired and wireless. The software modules 38 can be configured to send and receive data from a database (e.g., from a computer readable medium 36 including data sources 37a and data storage 37b that can comprise a database), and data can be received by the software modules 38 from at least one other source. For example, as described earlier, in some embodiments of the invention, using the system 30, the medical services tracking server system and method can be configured to receive one or more CCD from one or more medical providers for display to the user 31. Further, in some embodiments, patient data can be retrieved from one or more master patient index databases (e.g. a master patient database managed by a government entity and/or a third party provider such as insurance company or collective of insurance companies). In some further embodiments, data can be retrieved from the national register of drugs and pharmaceuticals.

In some embodiments, at least one of the software modules 38 can be configured within the system 30 to output data to at least one user 31 via at least one digital display (e.g., to a computer 40 comprising a digital display). In some embodiments, the system 30 as described can enable one or more users 31 to receive, analyze, input, modify, create and send data to and from the system 30, including to and from one or more enterprise applications 38 running on the system 30. Some embodiments include at least one user 31 coupled to a computer 40 accessing one or more modules of the medical services tracking server system including at least one enterprise applications 38 via a stationary I/O device 37c through a LAN 39a. In some other embodiments, the system 30 can enable at least one user 31 (through computer 40) accessing enterprise applications 38 via a stationary or mobile I/O device 37c through an internet 39a.

In some embodiments, the software modules 38 can include a server-based software platform that can include medical services tracking software modules suitable for hosting at least one user 31 account and at least one patient account or record. Further, some embodiments of invention includes the software modules 38 that can include at least one server-based software platform that can include medical services tracking software modules suitable for hosting at least at least one patient account or record. In some embodiments, using the system 30, the medical services tracking server system and method can manage multiple user accounts and/or multiple patient accounts. In some embodiments, the software modules 38 can include a server-based software platform that can include medical services tracking software modules suitable for hosting a plurality of user accounts accessible by multiple medical practitioners (e.g., doctors, physicians, surgeons, optometrists, ophthalmologists, podiatrists, dentists, etc.) In some embodiments of the invention, patient accounts can be accessible by the patient's medical practitioner and not shared with other medical practitioners holding one or more user accounts within the medical services tracking server system and method. In some further embodiments, one or more patient accounts can be accessible and shared by a user 31 associated with the patient account. For example, in some embodiments, a user 31 can grant access to at least one other user of the medical services tracking server system and method. In some embodiments, shared access can be at least partially restricted. For example, in some embodiments, shared access can be restricted to viewing at least a portion of the shared patient's account or record.

Any of the operations described herein that form part of the invention are useful machine operations. The invention also relates to a device or an apparatus for performing these operations. The apparatus can be specially constructed for the required purpose, such as a special purpose computer. When defined as a special purpose computer, the computer can also perform other processing, program execution or routines that are not part of the special purpose, while still being capable of operating for the special purpose. Alternatively, the operations can be processed by a general purpose computer selectively activated or configured by one or more computer programs stored in the computer memory, cache, or obtained over a network. When data is obtained over a network the data can be processed by other computers on the network, e.g. a cloud of computing resources.

The embodiments of the present invention can also be defined as a machine that transforms data from one state to another state. The data can represent an article, that can be represented as an electronic signal and electronically manipulate data. The transformed data can, in some cases, be visually depicted on a display, representing the physical object that results from the transformation of data. The transformed data can be saved to storage generally or in particular formats that enable the construction or depiction of a physical and tangible object. In some embodiments, the manipulation can be performed by a processor. In such an example, the processor thus transforms the data from one thing to another. Still further, the methods can be processed by one or more machines or processors that can be connected over a network. Each machine can transform data from one state or thing to another, and can also process data, save data to storage, transmit data over a network, display the result, or communicate the result to another machine. Computer-readable storage media, as used herein, refers to physical or tangible storage (as opposed to signals) and includes without limitation volatile and non-volatile, removable and non-removable storage media implemented in any method or technology for the tangible storage of information such as computer-readable instructions, data structures, program modules or other data.

Although method operations can be described in a specific order, it should be understood that other housekeeping operations can be performed in between operations, or operations can be adjusted so that they occur at slightly different times, or can be distributed in a system which allows the occurrence of the processing operations at various intervals associated with the processing, as long as the processing of the overlay operations are performed in the desired way.

It will be appreciated by those skilled in the art that while the invention has been described above in connection with particular embodiments and examples, the invention is not necessarily so limited, and that numerous other embodiments, examples, uses, modifications and departures from the embodiments, examples and uses are intended to be encompassed by the claims attached hereto. Various features and advantages of the invention are set forth in the following claims.

The invention claimed is:

1. A server system for aggregating and tracking medical delivery to a patient comprising;
   a computing device comprising at least one processor;
   a non-transitory computer-readable medium, having stored thereon, software instructions that when executed by the at least one processor of the computing device, cause the computing device to perform operations within a local or consumer device as part of a medical services tracking server system, the operations comprising at least:

associating the local or consumer device with at least one patient database or server;

establishing a dataflow comprising a delivery of patient data for at least one patient within a webpage or display rendered on the local or consumer device;

displaying a medical record dashboard comprising one or more windows including information received or derived from the at least one patient database or server, the medical record dashboard comprising a display on a single screen, using the one or more windows, of at least one of medical services, clinical data, examination findings, and diagnostic tests or procedures performed on a patient and a concurrent display on the single screen of information regarding a balance due on the patient's financial account, wherein the at least one of the medical services, the clinical data, the examination findings, and the diagnostic tests or procedures and the information regarding the balance due on the patient's financial account are arranged in rows or columns on the single screen according to at least one of a time and a date that the medical services, the clinical data, the examination findings, and the diagnostic tests or procedures were performed and the balance due on the patient's financial account on the at least one of the time and the date that the at least one of the medical services, the clinical data, the examination findings, and the diagnostic tests or procedures were performed, wherein the at least one of the time and the date is presented on the single screen in one direction in the rows and columns and the at least one of the medical services, the clinical data, the examination findings, and the diagnostic tests or procedures and the information regarding the balance due on the patient's financial account are presented on the single screen in another direction in the rows and columns;

generating at least one graphical representation indicative of at least a portion of the at least one of the medical services, the clinical data, the examination findings, the diagnostic tests or procedures and the information regarding the balance due on the patient's financial account, such that the at least one graphical representation when displayed on the single screen takes up less area on the single screen than the at least a portion of the information for which the at least one graphical representation was generated; and displaying at least one of the at least one generated graphical representation on the single screen in place of the information for which the graphical representation was generated, such that when a user selects the displayed graphical representation, at least one of medical services information, clinical data information, examination findings information, diagnostic test or procedure information and a financial ledger is displayed on the at least one or more windows in the single screen.

2. The server system of claim 1, wherein the operations include dynamically linking to at least one electronic medical records server system.

3. The server system of claim 2, wherein the operations cause the computing device to launch the medical services tracking server system from a user interface of the at least one electronic medical records server system on a display of the local or consumer device as directed by the user.

4. The server system of claim 1, wherein the operations further include providing the user edit access to the medical record dashboard to update or mark at least one medical data field based on at least one medical diagnosis.

5. The server system of claim 4, wherein the update or mark comprises an icon, the icon representative of at least one of a worsening medical condition, a stable medical condition, or an improving medical condition.

6. The server system of claim 1, wherein the graphical representation comprises a visual representation of at least one of items billed, not paid, partially paid and fully paid by at least one of insurance and a patient, or an outstanding amount from patient items not paid; and wherein a selection of the graphical representation by the user produces a display of a status of claim reimbursement with patient and insurance information.

7. The server system of claim 1, wherein the operations further include providing, on the medical record dashboard, at least one user-selectable link to a medical record, and wherein, when linked to, the medical record is displayed without leaving a display of the medical record dashboard.

8. The server system of claim 7, wherein the at least one user-selectable medical record comprises at least one test result or diagnosis from a procedural terminology code or any international classification of disease codes.

9. The server system of claim 7, wherein the medical record comprises at least one of visual acuity (VA), intraocular pressure (IOP), a photograph image, a visual field, a fluorescein angiography or optical coherence tomography (OCT) and photographic images of a patient's eyes.

10. The server system of claim 1, wherein the information related to the at least one of the medical services, the clinical data, the examination findings, the diagnostic tests or procedures and the information regarding the balance due on the patient's financial account is auto-populated based at least in part on information associated with data from at least one of a Digital Imaging and Communications in Medicine (DICOM) system, and data from a diagnostic or equipment used for treatment.

11. The server system of claim 1, wherein the at least one patient database or server comprises patient information from at least one of a medical service provider, a transition of care document or proactive care form, and a direct message.

12. The server system of claim 1, wherein the operations further include causing the computing device to display an instant message field configured to communicate information to the user.

13. The server system of claim 1, wherein any of the operations can include a self-destruct feature configured and arranged to erase any previously displayed information after a specified time period.

14. The server system of claim 1, wherein the operations further include:

auto-populating the medical record dashboard with information associated with at least one of a patient treatment or treatment summary, a diagnosis or diagnosis summary, patient feedback or a patient feedback summary, and other physician summaries or patient records.

15. The server system of claim 1, wherein the operations further include:

calculating at least one patient outcome based at least in part on patient information from at least one of a patient exam or exam summary, a diagnosis or diagnosis summary, patient feedback or a patient feedback summary, and other physician summaries and patient records.

16. The server system of claim 1, wherein the medical record dashboard further comprises quality measures.

17. The server system of claim 1, wherein the dataflow comprises a two-way transfer between the medical record dashboard and the at least one remote patient database or server.

18. The server system of claim 1, wherein the information regarding the balance due on the patients financial account comprises a financial ledger including billing and payment information.

19. The server system of claim 1, wherein the graphical representation provides access to the underlying information for which it was generated.

20. The server system of claim 1, wherein access to the underlying information is provided using a window that pops up over the single-screen.

21. The server system of claim 1, the operations further comprising auto-populating at least a portion of the medical record dashboard based on information associated with at least one of an unbilled medical service and an unbilled patient-related procedure.

22. The server system of claim 1, wherein the medical record dashboard further comprises at least one window that enables a user to view and edit at least one of summary information related to the patient, details of care provided to the patient, and medical diagnosis information.

23. The server system of claim 1, wherein the medical record dashboard provides shared access to the patient related medical records data by multiple medical practitioners.

24. The server system of claim 1, wherein the medical record dashboard lists multiple patients by date.

25. The server system of claim 1, wherein the medical record dashboard lists multiple visits for a patient by date.

26. The server system of claim 1, wherein the medical record dashboard includes a current day's plan for the patient.

27. A computer implemented medical services method comprising:
    establishing a dataflow for receiving patient related information from at least one patient database or server;
    displaying a medical record dashboard comprising one or more windows including information received or derived from the at least one patient database or server, the medical record dashboard comprising a display on a single screen, using the one or more windows of at least one of medical services, clinical data, examination findings, and diagnostic tests or procedures performed on a patient and a concurrent display on the single screen of information regarding a balance due on the patient's financial account,
    wherein the at least one of the medical services, the clinical data, the examination findings, and the diagnostic tests or procedures and the information regarding the balance due on the patient's financial account are arranged in rows and columns on the single screen according to at least one of a time and a date that the medical services, the data, the examination findings, and the diagnostic tests or procedures were performed and the information regarding the balance due on the patient's financial account on the at least one of the time and the date that the at least one of the medical services, the clinical data, the examination findings, and the diagnostic tests or procedures were performed,
    wherein the at least the one of the time and the date is presented on the single screen in one direction in the rows and columns and the at least one of the medical services, the clinical data, the examination findings, the diagnostic tests or procedures and the information regarding the balance due on the patient's financial account are presented on the single screen in another direction in the rows and columns;
    generating at least one graphical representation indicative of at least a portion of the at least one of the medical services, the clinical data, the examination findings, the diagnostic tests or procedures and the information regarding the balance due on the patient's financial account, such that the generated at least one graphical representation when displayed on the single screen takes up less area on the single screen than a portion of the information for which the at least one graphical representation was generated; and
    displaying at least one of the at least one generated graphical representation on the single screen in place of the information for which the graphical representation was generated, such that when a user selects the displayed graphical representation, at least one of medical services information, clinical data information, examination findings information, diagnostic test or procedure information and a financial ledger is displayed on the at least one or more windows in the single screen.

28. The computer-implemented method of claim 27, further comprising providing the user edit access to the medical record dashboard to update or mark at least one medical data field based on at least one of a summary of information related to the patient, details of care provided to the patient and a medical diagnosis.

29. The computer-implemented method of claim 28, wherein the update or mark comprises an icon, the icon representative of at least one of a worsening medical condition, a stable medical condition, and an improving medical condition.

30. The computer-implemented method of claim 27, wherein the graphical representation comprises a visual representation of at least one of items billed, not paid, partially paid and fully paid by insurance, and an outstanding amount from patient items not paid; and
    wherein a launch of the graphical representation produces a display of a status of claim reimbursement with patient and insurance information.

31. The computer-implemented method of claim 27, further comprising providing, on the medical record dashboard, at least one user-selectable link to a medical record, wherein the medical record comprises at least one test result or diagnosis from any procedural terminology code and any international classification of disease codes.

32. The computer-implemented method of claim 27, wherein the information related to the at least one of the medical service, the clinical data, the examination findings, the diagnostic tests or procedures and the information regarding the balance due on the patient's financial account is auto-populated based at least in part on information associated with data from a diagnostic or equipment used for treatment.

33. The computer-implemented method of claim 27, wherein the at least one patient database or server comprises patient information from at least one of a medical provider, a transition of care document, a proactive care form, and a direct message.

34. The computer-implemented method of claim 31, wherein the medical record comprises at least one of visual acuity (VA), intraocular pressure (IOP), a photograph image, a visual field, a fluorescein angiography or optical coherence tomography (OCT) and photographic images of a patient's eyes.

35. The computer-implemented method of claim 27, further comprising causing the computing device to display an instant message field configured to communicate information to the user.

36. The computer-implemented method of claim 27, wherein any of the operations can include a self-destruct feature configured and arranged to erase any previously displayed information after a specified time period.

37. The computer-implemented method of claim 27, further comprising:

auto-populating the medical record dashboard with information associated with at least one of a patient treatment or treatment summary, a diagnosis or diagnosis summary, patient feedback or a patient feedback summary, and other physician summaries or patient records.

38. The computer-implemented method of claim 27, further comprising:

calculating at least one patient outcome based at least in part on patient information from at least one of a patient treatment or treatment summary, a diagnosis or diagnosis summary, patient feedback or a patient feedback summary, and other physician summaries and patient records.

39. The computer-implemented method of claim 27, wherein the medical record dashboard further comprises quality measures.

40. The computer-implemented method of claim 27, wherein the dataflow comprises a two-way transfer between the medical record dashboard and the at least one remote patient database or server.

* * * * *